US006211228B1

(12) United States Patent
Rice et al.

(10) Patent No.: US 6,211,228 B1
(45) Date of Patent: Apr. 3, 2001

(54) COMPOSITIONS AND METHODS FOR TREATING MAST-CELL MEDIATED CONDITIONS

(75) Inventors: Ken Duane Rice, Palo Alto; Jeffrey Mark Dener, Daly City; Anthony Robert Gangloff, San Mateo; Elaine Yee-Lin Kuo, San Francisco, all of CA (US)

(73) Assignee: Axys Pharmaceuticals, Inc, South San Francisco, CA (US)

( * ) Notice: Subject to any disclaimer, the term of this patent is extended or adjusted under 35 U.S.C. 154(b) by 0 days.

(21) Appl. No.: 09/280,227

(22) Filed: Mar. 29, 1999

Related U.S. Application Data

(60) Division of application No. 08/522,157, filed on Sep. 14, 1995, now Pat. No. 6,022,969, which is a continuation-in-part of application No. 08/312,269, filed on Sep. 23, 1994, now abandoned.

(51) Int. Cl.[7] .................. A61K 71/335; C07C 321/12
(52) U.S. Cl. .................. 514/450; 514/252.1; 514/316; 514/211.06; 514/465; 514/479; 540/575; 544/357; 546/187; 560/25; 560/26; 549/347; 549/434; 128/28; 424/45
(58) Field of Search .................. 540/575; 544/357; 546/187; 560/25, 26; 549/347, 434; 514/211.06, 252.1, 316, 450, 465, 479

(56) References Cited

U.S. PATENT DOCUMENTS

| | | | |
|---|---|---|---|
| 4,220,646 | 9/1980 | Cotrel et al. | 424/250 |
| 4,746,737 | 5/1988 | Fujii et al. | 540/575 |

FOREIGN PATENT DOCUMENTS

| | | |
|---|---|---|
| 0 214 429 A1 | 1/1987 | (EP) . |
| 94/20527 | 9/1994 | (WO) . |
| 95/32945 | 12/1995 | (WO) . |

OTHER PUBLICATIONS

Castells et al., "Tryptase levels in nasal–lavage fluid as an indicator of the immediate allergic response," *J. Allergy Clin. Immunol.*, 82:348–355 (1988).
Caughey et al., "Substance P and Vasoactive Intestinal Peptide Degradation by Mast Cell Tryptase and Chymase," *J. Pharmacol. Exp. Ther.*, 244:133–137 (1988).
Caughey, "The Structure and Airway Biology of Mast Cell Proteinases," *Am. J. Respir. Cell Mol. Biol.* 4:387–394 (1991).
Chiu et al., "Gastric Cytoprotective Properties of SCH 32761, a Novel Antiulcer Agent," *Arch. Int. Pharmacodyn.* 270:128–140 (1984).
Cotrel et al., "Heterocyclic compounds and compositions containing them," *Chemical Abstracts* 85:4678m (1976).
Cotrel et al., "Heterocyclic compounds for pharmaceutical compositions," *Chemical Abstracts* 94:156973w (1981).

Farge et al., "Dithiepino[1,4][2,3–c]pyrrole derivatives and pharmaceutical compositions containing them," *Chemical Abstracts* 95:43190r (1981).
Franconi et al., "Mast Cell Tryptase and Chymase Reverse Airway Smooth Muscle Relaxation Induced by Vasoactive Intestinal Peptide in the Ferret," *J. Pharmacol. Exp. Ther.* 248(3):947–951 (1988).
Jeanmart et al., "Dithiepino[1,4][2,3–c]pyrrole derivatives," *Chemical Abstracts* 87:184560h (1977).
Kalenderian et al., "Elevated Histamine and Tryptase Levels in Smokers' Bronchoalveolar Lavage Fluid—Do Lung Mast Cells Contribute to Smokers' Emphysema?" *Chest* 94:119–123 (1988).
Larsen, "Experimental Models of Reversible Airway Obstruction," *The Lung: Scientific Foundations* 953–965 (1991).
Miller et al., "Cloning and Characterization of Complementary DNA for Human Tryptase," *J. Clin. Invest.* 86:864–870 (1990).
Miller et al., "Cloning and Characterization of Complementary DNA for Human Tryptase," *J. Clin. Invest.* 84:1188–1195 (1989).
Ruoss et al., "Mast Cell Tryptase Is a Mitogen for Cultured Fibroblasts," *J. Clin. Invest.* 88:493–499 (1991).
Schwartz et al., "Tryptase Levels as an Indicator of Mast–Cell Activation in Systemic Anaphylaxis and Mastocytosis," *J. Clin. Invest.* 83:175–179 (1989).
Sekizawa et al., "Mast Cell Tryptase Causes Airway Smooth Muscle Hyperresponsiveness in Dogs," *J. Clin. Invest.* 83:175–179 (1989).
Sturzebecher et al., "Inhibition of Human Mast Cell Tryptase by Benzamidine Derivatives," *Biol. Chem. Hoppe–Seyler* 373:1025–1030 (1992).
Tam et al., "Degradation of Airway Neuropeptides by Human Lung Tryptase," *Am. J. Respir., Cell Mol. Biol.* 3:27–32 (1990).
Tidwell et al., "Aromatic Amidines: Comparison of Their Ability to Block Respiratory Syncytial Virus Induced Cell Fusion and the Inhibit Plasmin, Urokinase, Thrombin, and Trypsin," *J. Med. Chem.* 26:294–298 (1983).

(List continued on next page.)

*Primary Examiner*—Richard L. Raymond
(74) *Attorney, Agent, or Firm*—Townsend and Townsend and Crew LLP

(57) ABSTRACT

Novel compounds, compositions and methods effective for the prevention and treatment of mast-cell mediated inflammatory disorders are described. The compounds, compositions and methods are effective for the prevention and treatment of inflammatory diseases associated with the respiratory tract, such as asthma and allergic rhinitis, as well as other types of immunomediated inflammatory disorders, such as rheumatoid arthritis, conjunctivitis and inflammatory bowel disease, various dermatological conditions, as well as certain viral conditions. The compounds comprise potent and selective inhibitors of the mast cell protease tryptase. The compositions for treating these conditions include oral, inhalant, topical and parenteral preparations as well as devices comprising such preparations.

30 Claims, 8 Drawing Sheets

OTHER PUBLICATIONS

Tidwell et al., "Suppression of Respiratory Syncytial Virus Infection in Cotton Rats by Bis(5–Amindino–2–Benzimidazolyl) Methane," *Antimicrobial Agents and Chemotherapy* 26:591–593 (1984).

Vanderslice et al., "Human mast cell tryptase: Multiple cDNAs and genes reveal a multigene serine protease family," *Proc. Natl. Acad. Sci. USA* 87:3811–3815 (1990).

Vanderslice et al., "Molecular Cloning of Dog Mast Cell Tryptase and Related Protease: Structural Evidence of a Unique Mode of Serine Protease Activation," *Biochemistry* 28:4148–4155 (1989).

Wanner et al., "Models of Airway Hyperresponsiveness," *Am. Rev. Respir. Dis.* 141:253–257 (1990).

Wenzel et al., "Activation of Pulmonary Mast Cells by Bronchoalveolar Allergen Challenge," *Am. Rev. Resp. Dis.* 141:1002–1008 (1988).

Figure 2

COMPOSITIONS AND METHODS FOR TREATING MAST-CELL MEDIATED CONDITIONS

This application is a divisional of U.S. patent application Ser. No. 08/522,157, filed Sep. 14, 1995, now U.S. Pat. No. 6,022,969, which is a CIP of Ser. No. 08/312,269, filed Sep. 23, 1994, now abandoned, the disclosures of which are incorporated by reference.

BACKGROUND OF THE INVENTION

1. Field of the Invention

This invention relates to compositions and methods effective for the prevention and treatment of mast-cell mediated inflammatory disorders. The invention includes compositions and methods effective for the prevention and treatment of inflammatory diseases associated with the respiratory tract, such as asthma and allergic rhinitis. The compositions and methods of the present invention are especially useful for preventing or treating the late phase bronchoconstriction and airway hyperresponsiveness associated with chronic asthma. In addition, the compositions and methods of the present invention have utility in treating other types of immunomediated inflammatory disorders, such as rheumatoid arthritis, conjunctivitis and inflammatory bowel disease, as well as various dermatological conditions. Further, the compositions and methods of the present invention have utility in the treatment of respiratory syncytial virus.

2. Description of the Background Art

Asthma is a complex disease involving multiple biochemical mediators for both its acute and chronic manifestations. Increasingly, asthma is recognized as an inflammatory disorder (see, e.g., Hood, et al., IMMUNOLOGY 2nd ed., Benjamin-Cummings 1984). Asthma frequently is characterized by progressive development of hyperresponsiveness of the trachea and bronchi to both immunospecific allergens and generalized chemical or physical stimuli. The hyperresponsiveness of asthmatic bronchiolar tissue is believed to result from chronic inflammation reactions, which irritate and damage the epithelium lining the airway wall and promote pathological thickening of the underlying tissue. Bronchial biopsy studies have indicated that even patients with mild asthma have features of inflammation in the airway wall.

One initiator of the inflammatory sequence is an allergic response to inhaled allergens. Leukocytes carrying IgE receptors, notably mast cells and basophils, but also including monocytes, macrophages, and eosinophils, are present in the epithelium and underlying smooth muscle tissues of bronchi where they are activated initially by binding of specific inhaled antigens to the IgE receptors. Activated mast cells release a number of preformed or primary chemical mediators of the inflammatory response and enzymes. Furthermore, numerous secondary mediators of inflammation are generated in situ by enzymatic reactions of activated mast cells, including superoxide and lipid derived mediators. In addition, several large molecules are released by degranulation of mast cells: proteoglycans, peroxidase, arylsulfatase B, and notably the proteases tryptase and chymotryptic proteinase (chymase). See DRUG THERAPY OF ASTHMA, pp. 1054–54.

This chemical release from mast cells probably accounts for the early bronchiolar constrictor response that occurs in susceptible individuals after exposure to airborne allergens. The early asthmatic reaction is maximal at around fifteen minutes after allergen exposure; recovery occurs over the ensuing one to two hours. In 25–35% of individuals, the early asthmatic reaction is followed by a further decline in respiratory function which begins within a few hours and is maximal between six and twelve hours post-exposure. This late asthmatic reaction is accompanied by a marked increase in the number of inflammatory cells infiltrating bronchiolar smooth muscle and epithelial tissues, and spilling into the airways. These cells include eosinophils, neutrophils, and lymphocytes, all of which are attracted to the site by release of mast cell derived chemotactic agents. The infiltrating cells themselves become activated during the late reaction phase. The late asthmatic response is believed to be a secondary inflammatory reaction mediated in part by the secretory activity of macrophages.

Tryptase is the major secretory protease of human mast cells and is proposed to be involved in neuropeptide processing and tissue inflammation. Mature human tryptase is a glycosylated, heparin-associated tetramer of heterogenous, catalytically active subunits. See, e.g., Vanderslice et al. *Proc. Natl. Acad. Sci. USA* 87:3811–3815 (1990); Miller et al. *J. Clin. Invest.* 86:864–870 (1990); Miller et al. *J. Clin. Invest.* 84:1188–1195 (1989); and Vanderslice et al. *Biochemistry* 28:4148–4155 (1989).

Tryptase is stored in mast cell secretory granules. After mast cell activation, human tryptase can be measured readily in a variety of biologic fluids. For example, after anaphylaxis, tryptase appears in the bloodstream, where it remains detectable for several hours. See Schwartz et al., *N. Engl. J. Med.* 316:1622–1626 (1987). Its appearance has been detected in samples of nasal and lung lavage fluid from atopic subjects challenged with specific antigen. See Castells and Schwartz, *J. Allerg. Clin. Immunol.* 82:348–355 (1988) and Wenzel, et al., *Am. Rev. Resp. Dis.* 141:563–568 (1988). Tryptase levels in lung lavage fluid obtained from atopic asthmatics increase after endobronchial allergen challenge. Some smokers of cigarettes have striking elevations of bronchoalveolar lavage fluid tryptase levels compared to nonsmoker control groups, a finding that provides some support for the hypothesis that release of proteinases from activated mast cells could contribute to lung destruction in smoker's emphysema. See Kalenderian, et al., *Chest* 94:119–123 (1988). In addition, tryptase has been shown to be a potent mitogen for fibroblasts, suggesting its involvement in pulmonary fibrosis and interstitial lung diseases. See Ruoss et al., *J. Clin. Invest.* 88:493–499 (1991).

Tryptase has been implicated in a variety of biological processes, including degradation of vasodilating and bronchorelaxing neuropeptides (see Caughey, et al., *J. Pharmacol. Exp. Ther.* 244:133–137 (1988); Franconi, et al., *J. Pharmacol. Exp. Ther.* 248:947–951 (1988); and Tam, et al., *Am. J. Respir. Cell Mol. Biol.* 3:27–32 (1990)) and modulation of bronchial responsiveness to histamine (see Sekizawa, et al., *J. Clin. Invest.* 83:175–179 (1989)). These studies suggest that tryptase possibly increases bronchoconstriction in asthma by destroying bronchodilating peptides.

Additionally, tryptase has been shown to cleave fibrinogen α-chains, as well as high molecular weight kininogen with a possible release of kinins and thus, may play a role with heparin as a local anticoagulant. The ability of tryptase to activate prostromelysin (pro-MMP-3) and procollagenase (pro-MMP-1) via MMP-3 suggests that tryptase also may be involved in tissue inflammation and remodeling. This finding also intimates that tryptase may play a role in joint destruction in rheumatoid arthritis. In addition, tryptase has been shown to cleave calcitonin gene-related peptide. As this peptide is implicated in neurogenic inflammation, tryptase could be a factor in the regulation of flare reaction in cutaneous neurogenic inflammation. See Caughey, *Am. J. Respir. Cell Mol. Biol.* 4:387–394 (1991).

Respiratory syncytial virus has also been found to be the cause of human respiratory disorders. This virus has been implicated as a leading cause of respiratory tract infection in infancy and childhood, such as bronchiolitis and bronchopneumonia. Certain compounds, specifically, aromatic amidino derivatives, generally recognized as inhibitors of trypsin, urokinase and plasmin, have been shown to be effective in blocking cell fusion induced by respiratory syncytial virus, and significantly reducing the yield of the virus. See R. R. Tidwell, et al., *J. Med. Chem.* 26(2):294–298 (1983), and Tidwell, et al., Antimicrobial Agents and Chemotherapy 26:591 (1984).

Mast cell mediated inflammatory conditions and syncytial viral infections are a growing public health concern. In particular, asthma has become a common chronic disease in industrialized countries. Therefore, it would be desirable to provide improved compositions and methods for providing effective treatment for these diseases.

SUMMARY OF THE INVENTION

The present invention provides symmetrical compounds of the formula:

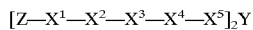

in which:

Z is amino, guanidino or amidino;

Y is optionally substituted cyclo($C_{3-14}$)alkylene or optionally substituted heterocyclo($C_{3-14}$) alkylene;

$X^1$ is optionally substituted ($C_{3-6}$)alkylene, optionally substituted oxa($C_{4-6}$)alkylene or —$X^6$—$X^7$—$X^8$— (wherein $X^7$ is optionally substituted phenylene, optionally substituted cyclo($C_{3-6}$)alkylene, or optionally substituted heterocyclo($C_{3-6}$)alkylene and $X^6$ and $X^8$ are optionally substituted ($C_{n6}$) alkylene and optionally substituted ($C_{n8}$) alkylene, respectively, wherein the sum of n6 and n8 is equal to 1, 2, 3 or 4, with the proviso that when Z is amino n6 is not 0); $X^2$ and $X^4$ are independently —C(O)—, —C(O)O—, —OC(O)—, —C(O)N($R^1$)—, —N($R^1$)C(O)—, —OC(O)N($R^1$)—, —N($R^1$)C(O)O—, —N($R^1$)C(O)N($R^1$)— or —OC(O)O— (wherein each $R^1$ is independently hydrogen, optionally substituted ($C_{1-8}$)alkyl or optionally substituted cyclo($C_{3-8}$)alkyl); $X^3$ is optionally substituted ($C_{1-8}$)alkylene, —$X^9$—$X^{10}$— or —$X^{10}$—$X^9$— (wherein $X^9$ is optionally substituted (Cn9)alkylene, wherein n9 is 0, 1 or 2, and $X^{10}$ is optionally substituted cyclo($C_{3-8}$)alkylene or optionally substituted heterocyclo($C_{3-8}$)alkylene, with the proviso that covalent bonds do not occur between hetero atoms contained within $X^{10}$ and hetero atoms contained within either $X^2$ or $X^4$); and $X^5$ is optionally substituted ($C_{n5}$)alkylene wherein n5 is 0, 1 or 2; and the pharmaceutically acceptable salts and prodrugs thereof.

The present invention provides unsymmetrical compounds of the formula:

in which $R^2$ and $R^3$ are independently Z—$X^1$—$X^2$—$X^3$—$X^4$—$X^5$— in which:

Z is amino, guanidino or amidino;

Y is optionally substituted cyclo($C_{3-14}$)alkylene or optionally substituted heterocyclo($C_{3-14}$)alkylene;

$X^1$ is optionally substituted ($C_{3-6}$)alkylene, optionally substituted oxa($C_{4-6}$)alkylene or —$X^6$—$X^7$—$X^8$— (wherein $X^7$ is optionally substituted phenylene, optionally substituted cyclo($C_{3-6}$)alkylene or optionally substituted heterocyclo($C_{3-6}$)alkylene and $X^6$ and $X^8$ are optionally substituted ($c_{n6}$)alkylene and optionally substituted ($C_{n8}$)alkylene, respectively, wherein the sum of n6 and n8 is equal to 1, 2, 3 or 4, with the proviso that when Z is amino n6 is not 0);

$X^2$ and $X^4$ are independently —C(O)—, —C(O)O—, —OC(O)—, —C(O)N($R^1$)—, —N($R^1$)C(O)—, —OC(O)N($R^1$)—, —N($R^1$)C(O)O—, —N($R^1$)C(O)N($R^1$)—, —OC(O)O— (wherein each $R^1$ is independently hydrogen, optionally substituted ($C_{1-8}$)alkyl or optionally substituted cyclo($C_{3-8}$)alkyl; $X^3$ is optionally substituted ($C_{1-8}$)alkylene, —$X^9$—$X^{10}$— or —$X^{10}$—$X^9$— (wherein $X^9$ is optionally substituted ($C_{n9}$)alkylene, wherein n9 is 0, 1 or 2, and $X^{10}$ is optionally substituted cyclo($C_{3-8}$)alkylene or optionally substituted heterocyclo($C_{3-8}$)alkylene, with the proviso that covalent bonds do not occur between hetero atoms contained within $X^{10}$ and hetero atoms contained within either $X^2$ or $X^4$);

$X^5$ is optionally substituted ($C_{n5}$)alkylene wherein n5 is 0, 1 or 2; with the proviso that $R^2$ and $R^3$ are not the same; and the pharmaceutically acceptable salts and prodrugs thereof.

The present invention provides pharmaceutical compositions comprising a compound of this invention or a pharmaceutically acceptable salt or salts thereof in admixture with one or more suitable excipients and said compositions further comprising a β-adrenergic agonist.

The present invention provides methods for treating an immunomediated inflammatory disorder of the respiratory tract of a mammal, said method comprising administering to said mammal a therapeutically effective amount of a compound of this invention or a pharmaceutically acceptable salt or salts thereof or a pharmaceutical composition containing said compound, salt or salts or said composition further comprising a β-adrenergic agonist.

The present invention provides a method for treating immunomediated inflammatory skin conditions, rheumatoid arthritis, conjunctivitis or syncytial virus infection in a mammal, said method comprising administering to said mammal a therapeutically effective amount of a compound of this invention or a pharmaceutically acceptable salt or salts thereof or a pharmaceutical composition containing said compound, salt or salts.

The pharmaceutical compositions of the present invention can be in a variety of forms including oral dosage forms, inhalable forms, as well as injectable and infusible solutions. When used in inhalant or aerosol form, the compounds of the present invention are used in combination with a pharmaceutically acceptable carrier solution or dry powder which can be converted into aerosol form. Similarly, when used in oral administration, the compounds of the present invention are used in combination with a pharmaceutically acceptable carrier suitable for such oral administration. When used for the treatment of immunomediated inflammatory skin conditions, the compounds of the present invention are used in combination with a non-toxic, pharmaceutically acceptable topical carrier. The compounds of the present invention can be used in combination with antiinflammatories or other asthma therapies, such as β-adrenergic agonists, antiinflammatory corticosteroids, anticholinergics, bronchodilators such as methyl xanthenes and the like.

The compounds described herein are useful for the prevention and treatment of immunomediated inflammatory disorders, and particularly those associated with the respiratory tract, including asthma, and particularly the hyperresponsiveness phase associated with chronic asthma, and allergic rhinitis. Thus, the present invention also provides a method for treating immunomediated inflammatory disorders wherein a patient having an immunomediated inflammatory disorder is administered a therapeutically effective dose or amount of a compound of the present invention. Further, the compounds described herein are useful for treating syncytial viral infections.

BRIEF DESCRIPTION OF THE DRAWINGS

FIG. 2 is a bar chart showing the airway hyperresponsiveness (measured as PC400) of antigen-challenged sheep treated with cis-1,5-cyclooctylene bis[4-(4-guanidinobenzylcarbamoyl)-1-piperazinecarboxylate] (Compound 3) by aerosol administration of 3, 50 µg doses, versus sheep treated with a control.

DESCRIPTION OF THE PREFERRED EMBODIMENT

I. Definitions

Figure 1:
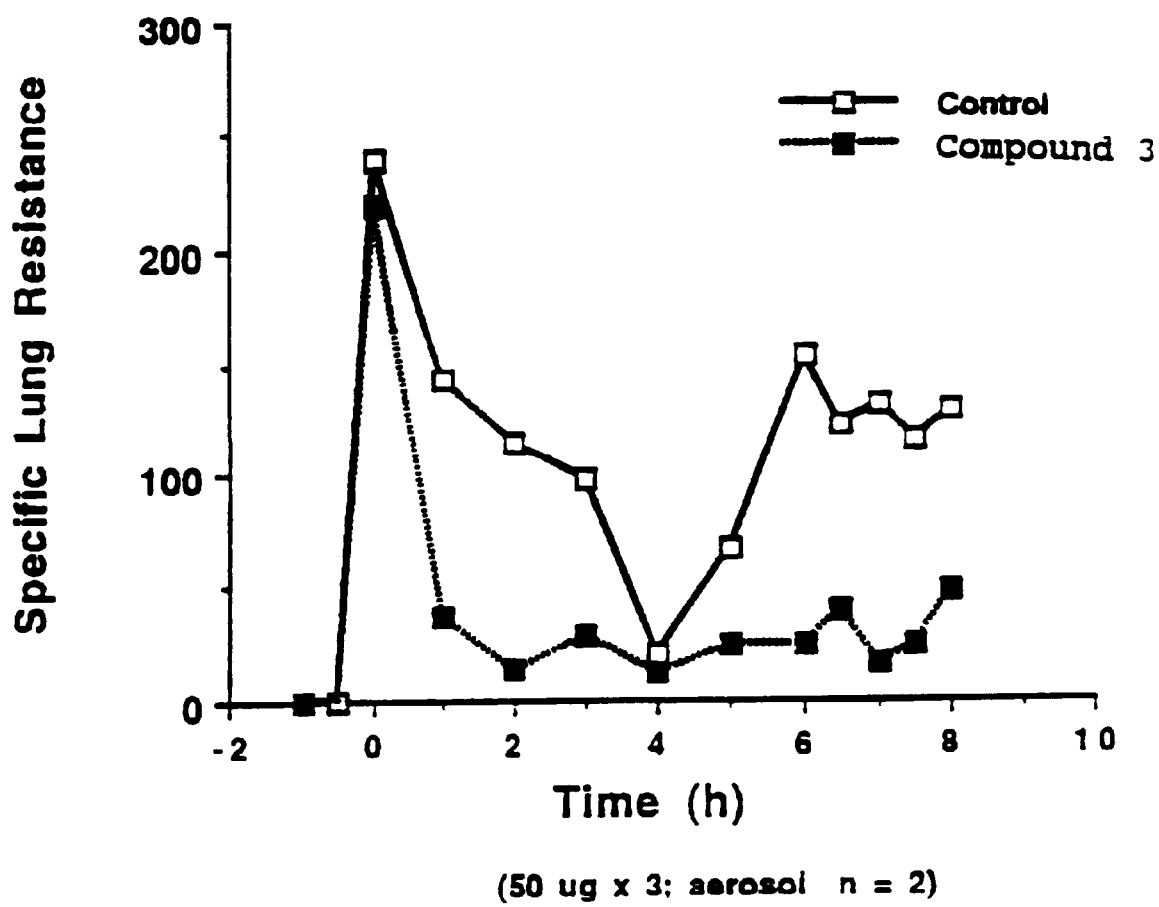
FIG. 1 is a graphical representation of the Specific Lung Resistance (SRL) as a function of time (in hours) of antigen-challenged sheep treated with cis-1,5-cyclooctylene bis[4-(4-guanidinobenzylcarbamoyl)-1-piperazinecarboxylate] (Compound 3) by aerosol administration of 3, 50 µg doses, versus sheep treated with a control.
Figure 3:
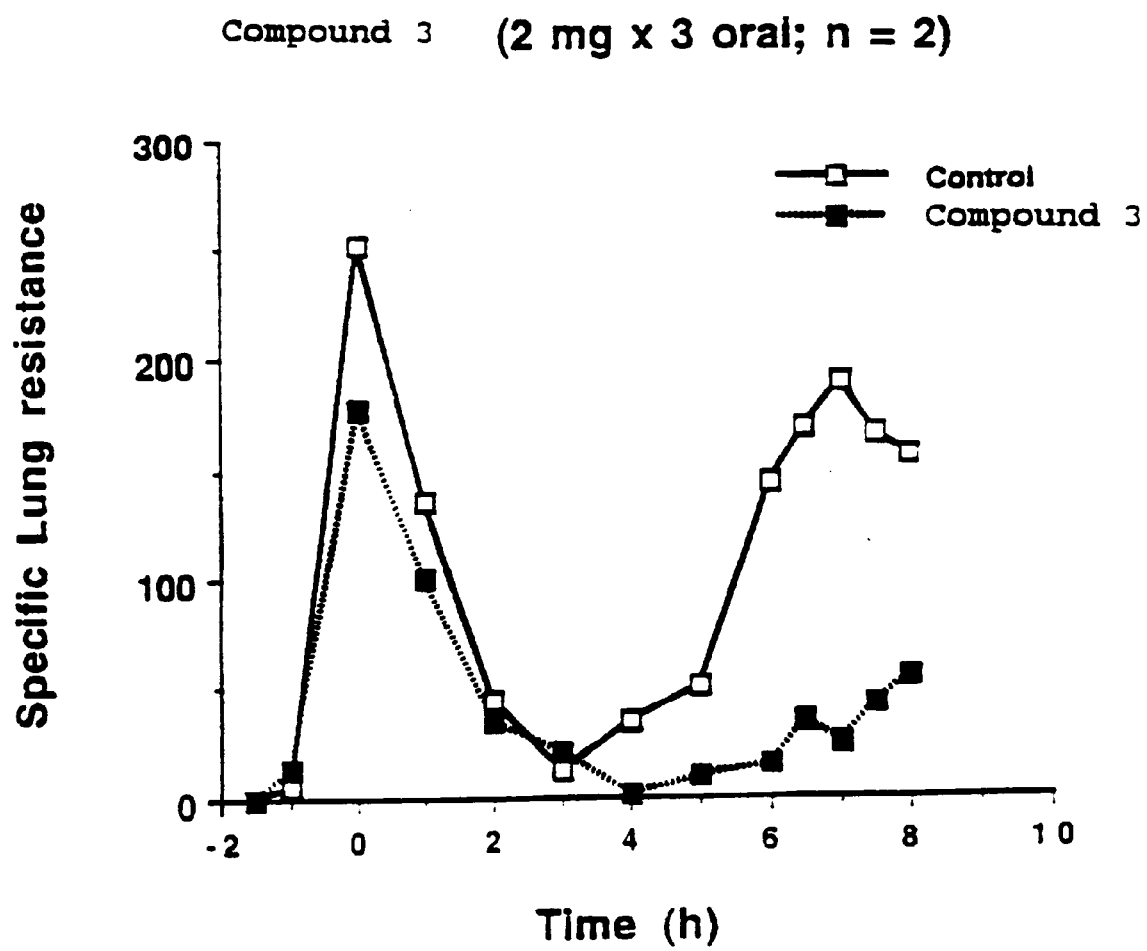
FIG. 3 is a graphical representation of the Specific Lung Resistance (SRL) as a function of time (in hours) of antigen-challenged sheep treated with cis-1,5-cyclooctylene bis[4-(4-guanidinobenzylcarbamoyl)-1-piperazinecarboxylate] (Compound 3) by oral administration of 3, 2 mg doses, versus sheep treated with a control.
Figure 4:
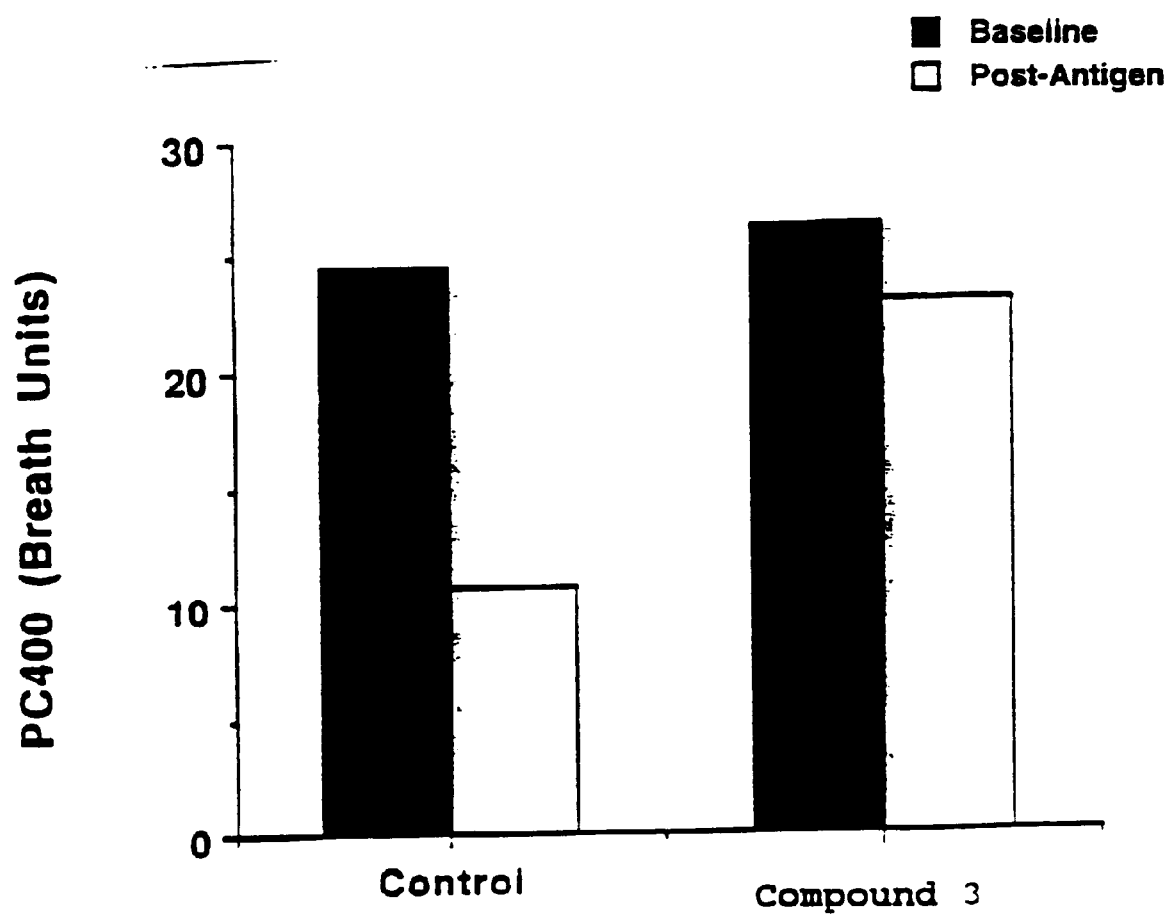
FIG. 4 is a bar chart showing the airway hyperresponsiveness (measured as PC400) antigen-challenged sheep treated with cis-1,5-cyclooctylene bis[4(4-guanidinobenzylcarbamoyl)-1-piperazinecarboxylate] (Compound 3) by oral administration of 3, 2 mg doses, versus sheep treated with a control.

The following definitions are set forth to illustrate and define the meaning and scope of the various terms used to describe the invention herein.

"Immunomediated inflammatory disorder" includes generally those diseases associated with mast cell mediator release and susceptible to treatment with a tryptase inhibitor. Examples of such disorders include diseases of immediate type hypersensitivity such as asthma, allergic rhinitis, urticaria and angioedema, and eczematous dermatitis (atopic dermatitis), and anaphylaxis, as well as hyperproliferative skin disease, peptic ulcers, inflammatory bowel disorder, ocular and vernal conjunctivitis, rheumatoid arthritis, inflammatory skin conditions, and the like.

"Hyperresponsiveness" refers to late phase bronchoconstriction and airway hyperreactivity associated with chronic asthma. Hyperresponsiveness of asthmatic bronchiolar tissue is believed to result from chronic inflammation reactions, which irritate and damage the epithelium lining the airway wall and promote pathological thickening of the underlying tissue.

"Halogen" refers to fluorine, bromine, chlorine, and iodine atoms.

"Hydroxyl" refers to the group —OH.

"Amino" refers to the group —NH$_2$.

"Oxa" as used herein refers to the divalent oxygen group —O—.

"Thiol" or "mercapto" refers to the group —SH.

The term "(C$_{1-8}$)alkoxy" denotes the group —OR, where R is (C$_{1-8}$)alkyl, substituted (C$_{1-8}$)alkyl, aryl, substituted aryl, aralkyl or substituted aralkyl as defined below.

"Alkyl", as in (C$_{1-4}$)alkyl or (C$_{1-8}$)alkyl, refers to straight or branched saturated hydrocarbon radical having from one to the number of carbon atoms designated. This term is further exemplified by such groups as methyl, ethyl, n-propyl, i-propyl, n-butyl, t-butyl, i-butyl,i-pentyl, n-pentyl, hexyl and the like. "Optionally substituted (C$_{1-8}$) alkyl" refers to an alkyl radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from (C$_{1-8}$)alkyl, (C$_{3-8}$) cycloalkyl, aryl, aryl(C$_{1-4}$)alkyl, acyl, (C$_{1-8}$)alkyloxy, aryloxy, cyclo(C$_{3-8}$)alkyloxy, aryl(C$_{1-4}$)alkyloxy, (C$_{1-8}$) alkylthio, arylthio, cyclo(C$_{3-8}$)alkylthio, aryl(C$_{1-4}$)alkylthio, acyloxy and the like.

"Cycloalkyl", as in cyclo(C$_{3-8}$)alkyl, refers to a saturated monocyclic hydrocarbon having the number of carbon atoms designated. This term is further exemplified by such groups as cyclopropyl, cyclobutyl, cyclopentyl, cyclohexyl and the like. "Optionally substituted cyclo(C$_{3-8}$)alkyl" refers to a cycloalkyl radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from (C$_{1-8}$)alkyl, cyclo(C$_{3-8}$)alkyl, aryl, aryl (C$_{1-4}$)alkyl, acyl, (C$_{1-8}$)alkyloxy, aryloxy, cyclo(C$_{3-8}$) alkyloxy, aryl(C$_{1-4}$)alkyloxy, (C$_{1-8}$)alkylthio, arylthio, cyclo (C$_{3-8}$)alkylthio, aryl(C$_{1-4}$)alkylthio, acyloxy and the like.

"Aryl" refers to an organic radical derived from an aromatic hydrocarbon containing 6 to 14 carbon atoms and includes monocyclic or condensed carbocyclic aromatic rings such as phenyl, naphthyl, anthracenyl, phenanthrenyl and the like. "Optionally substituted aryl" refers to an aryl radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from $(C_{1-8})$alkyl, cyclo$(C_{3-8})$alkyl, aryl, aryl$(C_{1-4})$alkyl, acyl, $(C_{1-8})$alkyloxy, aryloxy, cyclo$(C_{3-8})$alkyloxy, aryl$(C_{1-4})$alkyloxy, $(C_{1-8})$alkylthio, arylthio, cyclo$(C_{3-8})$alkylthio, aryl$(C_{1-4})$alkylthio, acyloxy and the like.

"Alkyloxy", as in $(C_{1-3})$alkyloxyl or $(C_{1-8})$alkyloxy, denotes the group —OR, wherein R is optionally substituted alkyl as defined above.

"Aryloxy", "cycloalkyloxy" and "aryl$(C_{1-4})$alkyloxy" denote the group —OR, wherein R is optionally substituted aryl, optionally substituted cycloalkyl and optionally substituted aryl$(C_{1-4})$alkyl, respectively, as defined above.

"Alkylthio" denotes the group —SR, wherein which R is optionally substituted alkyl as defined above.

"Arylthio", "cycloalkylthio" and "aryl$(C_{1-4})$alkylthio" denote the group —SR, wherein R is optionally substituted aryl, optionally substituted cycloalkyl or optionally substituted aryl$(C_{1-4})$alkyl, respectively, as defined above.

"Acyl" denotes the group —C(O)R, wherein R is optionally substituted alkyl, optionally substituted cycloalkyl or optionally substituted aryl as defined above.

"Acyloxy" denotes the group —OC(O)R, wherein R is optionally substituted alkyl, optionally substituted cycloalkyl or optionally substituted aryl as defined above.

"Amino$(C_{1-4})$alkyl", "amino$(C_{1-4})$alkyloxy" and "amino$(C_{1-4})$alkenyl" refer to an alkyl, alkyloxy or alkenyl radical as defined above, wherein an amino group is attached to the terminal ($\Omega$—) carbon of the radical.

"Alkylene", for the purposes of this application, refers to a saturated or unsaturated, divalent radical having the number of carbon atoms designated. This term is further exemplified by such groups as methylene (—CH$_2$—), ethylene (—CH$_2$CH$_2$—), trimethylene (—CH$_2$CH$_2$CH$_2$—) and the like. "Optionally substituted alkylene" refers to a divalent radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from $(C_{1-8})$alkyl, $(C_{3-8})$cycloalkyl, aryl, aryl$(C_{1-4})$alkyl, acyl, $(C_{1-8})$alkyloxy, aryloxy, cyclo$(C_{3-8})$alkyloxy, aryl$(C_{1-4})$alkyloxy, $(C_{1-8})$ alkylthio, arylthio, cyclo$(C_{3-8})$ alkylthio, aryl $(C_{1-4})$alkylthio, acyloxy and the like.

"Oxaalkylene," as in oxa$(C_{4-6})$alkylene, denotes the divalent radical —R—O—R'—, wherein R and R' are independently alkylene as defined above, having the number of atoms designated. This term is further exemplified by such groups as 2-oxatrimethylene (—CH$_2$—O—CH$_2$—), 2-oxatetramethylene (—CH$_2$—OCH$_2$CH$_2$—), 3-oxatetramethylene (—CH$_2$CH$_2$—O—CH$_2$—), 3-oxapentamethylene (—CH$_2$CH$_2$—O—CH$_2$CH$_2$—), 3-oxahexylmethylene (—CH$_2$CH$_2$—O—CH$_2$CH$_2$CH$_2$—), and the like. "Optionally substituted oxaalkylene" refers to a divalent radical as defined above, optionally substituted with one or more functional groups such as halogen, hydroxyl, amino, —NRR' (wherein R and R' are independently hydrogen, optionally substituted alkyl, optionally substituted cycloalkyl, optionally sybstituted aryl or optionally substituted acyl), mercapto or an optionally substituted group selected from $(C_{1-8})$alkyl, cyclo$(C_{1-4})$alkyl, aryl, aryl$(C_{1-4})$alkyl, acyl, $(C_{1-8})$alkyloxy, aryloxy, cyclo$(C_{3-8})$alkyloxy, aryl$(C_{1-4})$alkyloxy, $(C_{1-8})$alkylthio, arylthio, cyclo $(c_{3-8})$alkylthio, aryl$(C_{1-4})$alkylthio, acyloxy and the like.

"Cycloalkylene," as in cyclo$(C_{3-14})$alkylene, for the purposes of this application, refers to a cyclic or polycyclic, saturated or nonaromatic unsaturated divalent radical having from 3 to the number of carbon atoms indicated. This term is further exemplified by such groups as cyclopropylene, cyclobutylene, cyclopentylene, cyclohexylene, cyclohexenylene, bicyclohexylene, bicyclohexenylene, cyclooctylene and the like. "Optionally substituted cycloalkylene" refers to a divalent radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from $(C_{1-8})$alkyl, $(C_{3-8})$ cycloalkyl, aryl, aryl$(C_{1-4})$alkyl, acyl, $(C_{1-8})$alkyloxy, aryloxy, cyclo$(C_{3-8})$ alkyloxy, aryl$(C_{1-4})$alkyloxy, $(C_{1-8})$ alkylthio, arylthio, cyclo$(C_{3-8})$alkylthio, aryl$(C_{1-4})$alkylthio, acyloxy and the like.

"Heterocycloalkylene", for the purposes of this application, refers to a cyclic or polycyclic, saturated or nonaromatic unsaturated divalent radical having from 3 to the number of atoms indicated, one or more of which are herero atoms chosen from N, O or S. This term is further exemplified by such groups as 1,5-dioxaoctylene, 4,8-dioxabicyclo[3.3.0]octylene and the like. "Optionally substituted heterocycloalkylene" refers to a divalent radical as defined above optionally substituted with one or more functional groups such as halogen, hydroxyl, amino, —NRR' (wherein R and R' are independently hydrogen, optionally substituted alkyl, optionally substituted cycloalkyl, optionally substituted aryl or optionally substituted acyl), mercapto or an optionally substituted group selected from $(C_{1-8})$alkyl, $(C_{3-8})$cycloalkyl, aryl, aryl$(C_{1-4})$ alkyl, acyl, $(C_{1-8})$alkyloxy, aryloxy, cyclo$(C_{3-8})$alkyloxy, aryl$(C_{1-4})$alkyloxy, $(C_{1-8})$ alkylthio, arylthio, cyclo$(C_{3-8})$ alkylthio, aryl $(C_{1-4})$alkylthio, acyloxy and the like.

"Pharmaceutically acceptable salt" refers to those salts which retain the biological effectiveness and properties of the parent compound and which are not biologically or otherwise undesirable.

"Prodrug" refers to a compound which, upon administration, undergoes chemical conversion by in vivo metabolic processes.

"Optionally" refers to an event or circumstance which may or may not occur, and the description includes instances when the event or circumstance occurs and when it does not. For example, the phrase "optionally substituted $(C_{1-8})$alkyl" refers to an alkyl group which may or may not contain further substitutions. Both circumstances would fall within the scope of the present invention.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds of the present invention may have one or more asymmetrical carbon atoms and therefore include various stereoisomers. All stereoisomers are included within the scope of the invention.

"Treatment" or "treating" refers to any administration of a compound of the present invention in vitro or in vivo and includes:

(i) inhibiting the symptoms of the disease; and/or (ii) lessening or inhibiting the long term effects of the disease.

The compounds of this invention are named in accordance with acceptable nomenclature rules generally consistent with "Chemical Abstracts". For example, the compound in which n5 is 0, Z—X$^1$— is 4-guanidinobenzyl, X$^2$ is —NHC(O)—, X$^3$ is 1,4-piperazinylene, X$^4$ is —C(O)O— and Y is cis-1,5-cyclooctylene, is named cis-1,5-cyclooctylene bis[4 (4-guanidinobenzylcarbamoyl)-1-piperazinecarboxylate]; the compound in which n5 is 1, Z—X$^1$— is trans-4-aminomethylcyclohexylmethyl, X$^2$ is —NHC(O)—, X$^3$ is 1,4-piperazinylene, X$^4$ is —C(O)O— and Y is trans-1,4-cyclohexylene is named trans-1,4-cyclohexylenedimethylene bis[4-(trans-4-aminomethylcyclohexylmethylcarbamoyl)-1-piperazinecarboxylate]; the compound in which n5 is 0, Z—X$^1$is 4-(2-aminoethyl)phenyl, X$^2$ is —C(O)—, X$^3$ is 1,4-piperazinylene, X$^4$ is —C(O)O— and Y is cis-1,5-cyclooctylene is named cis-1,5-cyclooctylene bis{4-[4(2-aminoethyl)benzoyl]-1-piperazinecarboxylate}; and the compound in which n5 is 0, Z—X$^1$— is trans-4-aminomethylcyclohexyl, x$^2$ is —NHC(O)O—, X$^3$ is ethylene, X$^4$ is N(CH$_3$)C(O)O— and Y is cis-1,5-cyclooctylene is named cis-1,5-cyclooctylene bis {N-2-(trans-4-aminomethylcyclohexylaminoformyloxy)ethyl-N-methylaminocarboxylate.

II. Compounds

The present invention provides symmetrical compounds of the formula:

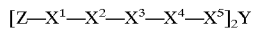

in which:

Z is amino, guanidino or amidino;

Y is optionally substituted cyclo(C$_{3-14}$)alkylene or optionally substituted heterocyclo(C$_{3-14}$)alkylene;

X$^1$ is optionally substituted (C$_{3-6}$)alkylene, optionally substituted oxa(C$_{4-6}$)alkylene or —X$^6$—X$^7$—X$^8$— (wherein X$^7$ is optionally substituted phenylene, optionally substituted cyclo(C$_{3-6}$)alkylene or optionally substituted heterocyclo(C$_{3-6}$)alkylene and X$^6$ and X$^8$ are optionally substituted (C$_{n6}$)alkylene and optionally substituted (C$_{n8}$)alkylene, respectively, wherein the sum of n6 and n8 is equal to 1, 2, 3 or 4, with the proviso that when Z is amino n6 is not 0); X$^2$ and X$^4$ are independently —C(O)—, —C(O)O—, —OC(O)—, —C(O)N(R$^1$)—, —N(R$^1$)C(O)—, —OC(O)N(R$^1$)—, —N(R$^1$)C(O)O—, —N(R$^1$)C(O)N(R$^1$)— or —OC(O)O—(wherein each R$^1$ is independently hydrogen, optionally substituted (C$_{1-8}$)alkyl or optionally substituted cyclo(C$_{38}$)alkyl); X$^3$ is optionally substituted (C$_{1-8}$)alkylene, —X$^9$—X$^{10}$— or —X$^{10}$—X$^9$— (wherein X$^9$ is optionally substituted (C$_{n9}$)alkylene, wherein n9 is 0, 1, 2, and X$^{10}$ is optionally substituted cyclo(C$_{3-8}$)alkylene or optionally substituted heterocyclo(C$_{3-8}$)alkylene, with the proviso that covalent bonds do not occur between hetero atoms contained within X$^{10}$ and hetero atoms contained within either X$^2$ or X$^4$); and X$^5$ is optionally substituted (C$_{n5}$)alkylene wherein n5 is 0, 1, 2; and the pharmaceutically acceptable salts thereof.

While the broadest definition of this invention is set forth in the Summary of the invention certain compounds of the invention are preferred. For example, generally preferred are those compounds in which Z is amino, n6 is 1 or 2, n8 is 1 and X$^6$ is 1,4-phenylene, 1,4-cyclohexylene, 1,4-bicyclo[2.2.2]octylene, 1,4-bicyclo[2.2.1]heptylene, 1,3-phenylene, 1,3-cyclohexylene, 1,3-bicyclo[2.2.2]octylene, 1,3-bicyclo[2.2.1]heptylene, or Z is guanidino or amidino, n6 is 0, n8 is 1 and X$^6$ is 1,4-phenylene or 1,3-phenylene; X$^2$ is —C(O)—, —C(O)NH—, or —NHC(O)O—; X$^3$ is 1,4-piperazinylene, 1,4-piperidylene, 1,4-perhydro-7H-1,4-diazepinylene or —X$^9$—X$^{10}$— (wherein X$^9$ is methylene and X$^{10}$ is 1,4-piperidylene) and X$^4$ is —C(O)— or —C(O)O—; or X$^3$ is (C$_{1-4}$)alkyene and X$^4$ is —N(R$^1$)C(O)O— (wherein R$^1$ is hydrogen or methyl); and Y is cyclooctylene, cyclohexylene, cyclopentylene, cis-decahydronaphthylene, transdecahydronaphthylene, perhydrophenanthrene, bicyclo[2.2.1]heptylene, bicyclo[2.2.2]octylene, bicyclo[3.3.1]nonylene, dioxabicyclo[3.3.0]octylene or tetracyclo[3.3.1.1$^{3,7}$]decylene.

More preferred are those compounds in which Z is amino, n6 and n8 are each 1 and X$^1$ is trans-1,4-cyclohexylene or Z is guanidino or amidino, n6 is 0, n8 is 1 and X$^1$ is 1,4-phenylene; X$^2$ is —C(O)— or —NHC(O)—; X$^3$ is 1,4-piperazinylene; X$^4$ is —C(O)O—; and n5 is 0 and Y is cis-1,5-cyclooctylene or n5 is 2 and Y is trans-cyclohexylene.

Examples of especially preferred compounds include: trans-1,4-cyclohexylenedimethylene bis(4-guanidinobenzylcarbamoylmethylaminocarboxylate), alternatively written in IUPAC nomenclature as 1,1'-trans-1,4-bis(4-cyclohexylenedimethylene bis[N-(p-guanidylbenzyl) glycinamide)-(N)-(α)-carboxylate];

cis-1,5-cyclooctylene bis(4-guanidinobenzylcarbamoylmethyl aminocarboxylate), alternatively written in IUPAC nomenclature as 1,1'-cis-1,5-cyclooctylene bis[N-4-(p-guanidylbenzyl) glycinamide)-(N)-α)-carboxylate];

cis-1,5-cyclooctylene bis[4-(4-guanidinobenzylcarbomoyl)-1-piperazinecarboxylate];

cis-1,5-cyclooctylene bis[4-(trans-4-aminomethylcyclohexyl methylcarbamoyl)-1-piperazinecarboxylate]; and cis-1,5-cyclooctylene bis[4-(4-guanidinophenylacetyl)-1-piperazinecarboxylate].

Generally, the compounds of the invention are synthesized using standard techniques and reagents. It will be noted that the linkages between the various groups, X$^1$, X$^2$, X$^3$, X$^4$ and X$^5$ comprise carbons linked to the nitrogen of an amide or carbamate, the oxygen of a carbamate or urea or the carbon of a carbonyl. Those of skill in the art will recognize that methods and reagents for forming these bonds are well known and readily available. See, e.g., March, ADVANCED ORGANIC CHEMISTRY, 4th Ed. (Wiley 1992), Larock, COMPREHENSIVE ORGANIC TRANSFORMATIONS (VCH 1989); and Furniss, et al., VOGEL'S TEXTBOOK OF PRACTICAL ORGANIC CHEMISTRY 5th ed. (Longman 1989), each of which is incorporated herein by reference. It will also be appreciated that any functional groups present may require protection and deprotection at different points in the synthesis of the compounds of the invention. Those of skill in the art will also recognize that such techniques are well known (see, e.g., Green and Wuts, PROTECTIVE GROUPS IN ORGANIC CHEMISTRY (Wiley 1991), also incorporated herein by reference).

The various groups $X^1$, $X^2$, $X^3$, $X^4$ and $X^5$ which comprise the compounds of this invention can be assembled individually or as larger combinations thereof. For example, compounds of the invention wherein $X^3$ is methylene and $X^4$ is —NHC(O)O— can be prepared by first reacting an appropriate cycloalkylenediol (e.g., cis-1,5-cyclooctanediol, trans-1,4-cyclohexylenedimethanol, etc.) with an excess of a suitable isocyanatoacetate to form the formyloxy linkage between $X^4$ and $X^5$, or Y when n5 is 0, hydrolyzing to give the corresponding dicarboxylic acid and then reacting the dicarboxylic acid with an appropriate protected amine (e.g., 4-tert-butoxycarbonylaminobenzylamine, etc.) in the presence of a suitable coupling agent.

Alternatively, an appropriate cycloalkylenediol is converted to a corresponding bis-chloroformate by treating with phosgene which is reacted with an appropriate mono-protected diamine to form a formyloxy linkage between $X^3$ and $X^5$, or Y when n5 is 0, deprotecting to give the corresponding intermediate with two reactive amines and then reacting the unprotected intermediate with an appropriate protected isocyanate (e.g., 4-tert-butoxycarbonylaminophenylmethyl isocyanate, etc.), deprotecting and performing any necessary last step reaction (e.g., converting an aminophenyl group to a guanidinophenyl). Compounds of the invention in which $X^2$ is —C(O)— can be prepared by proceeding as above but reacting the unprotected intermediate with an appropriate carboxylic acid (e.g., 4-aminobenzoic acid, 4-aminomethylbenzoic acid, etc.). Compounds of the invention in which Z is substituted with guanidino can be prepared from a corresponding bis(amine) by reacting with amino cyanamide. Compounds of the invention in which Z is amidino can be prepared from a corresponding bis(nitrile) by treating with hydrogen chloride and ethanol followed by exposure to ammonia. The reaction steps described in this and the preceding paragraph can be performed by methods known to those of ordinary skill in the art.

The present invention provides unsymmetrical compounds of the formula:

in which $R^2$ and $R^3$ are independently Z—$X^1$—$X^2$—$X^3$—$X^4$—$X^5$ in which:

Z is amino, guanidino or amidino;

Y is optionally substituted cyclo($C_{3-14}$)alkylene or optionally substituted heterocyclo($C_{3-14}$)alkylene;

$X^1$ is optionally substituted ($C_{3-6}$)alkylene, optionally substituted oxa($C_{4-6}$)alkylene or —$X^6$—$X^7$—$X^8$— (wherein $X^7$ is optionally substituted phenylene, optionally substituted cyclo($C_{3-6}$)alkylene or optionally substituted heterocyclo($C_{3-6}$)alkylene and $X^6$ and $X^8$ are optionally substituted ($C_{n6}$)alkylene and optionally substituted ($C_{n8}$)alkylene, respectively, wherein the sum of n6 and n8 is equal to 1, 2, 3 or 4, with the proviso that when Z is amino n6 is not 0); $X^2$ and $X^4$ are independently —C(O)—, —C(O)O—, —OC(O)—, —C(O)N($R^1$)—, —N($R^1$)C(O)—, —OC(O)N($R^1$)—, —N($R^1$)C(O)O— (wherein each $R^1$ is independently hydrogen, optionally substituted ($C_{1-8}$)alkyl or optionally substituted cyclo($C_{4-8}$)alkyl); $X^3$ is optionally substituted ($C_{1-8}$)alkylene, —$X^9$—$X^{10}$—, or —$X^{10}$—$X^9$—(wherein $X^9$ is optionally substituted ($C_{n9}$)alkylene, wherein n9 is 0, 1 or 2, and $X^{10}$ is optionally substituted cyclo($C_{3-8}$)alkylene or optionally substituted heterocyclo($C_{3-8}$)alkylene, with the proviso that covalent bonds do not occur between hetero atoms contained within $X^{10}$ and hetero atoms contained within either $X^2$ or $X^4$); $X^5$ is optionally substituted ($C_{n5}$)alkylene wherein n5 is 0, 1 or 2; with the proviso that $R^2$ and $R^3$ are not the same; and the pharmaceutically acceptable salts thereof.

The unsymmetrical compounds of the invention can be prepared by proceeding analogously to that described herein for preparing symmetrical compounds of the invention but introducing various $X^1$, $X^2$, $X^3$, $X^4$, and $X^5$ groups independently. For example, compounds of the invention in which —$X^4$—$X^5$— or $R^2$ and $R^3$ are the same and the Z—$X^1$—$X^2$—$X^3$— of $R^2$ and $R^3$ are different can be prepared by converting an appropriate cycloalkylenediol to a corresponding bis-chloroformate, reacting the bis-chloroformate with one molar equivalent of an appropriate mono-protected diamine to give the corresponding monochloroformate, reacting the monochloroformate with an appropriate mono-protected diamine to give a compound of the formula P—$X^4$—$X^5$—Y—$X^5$—$X^4$—P', wherein P and P are each chemically distinct protecting groups (e.g., tert-butoxycarbonyl and benzyl), orthogonally removing one or the other protecting group and then proceeding as described above for the preparation of the symmetrical compounds of the invention. Appropriate protecting groups and the methods for selectively deprotecting are known to those of ordinary skill in the art. Those of skill in the art would recognize that analogous methods can be employed to prepare other unsymmetrical compounds of the invention in which the Z, $X^1$, $X^2$, $X^3$, $X^4$ and $X^5$ of $R^2$ and $R^3$ independently vary.

In some cases, $X^3$ will be selected from the group consisting of heterocycloalkylene and substituted heterocycloalkylene, e.g., piperazine, homopiperazine and hydroxypiperidine. These groups may be added individually in analogy to the above methodologies or formed in situ from appropriately functionalized alkylenes using commonly known synthetic techniques such as those described in March, Larock of Furniss, supra.

Those of skill in the art will also appreciate that the linking group —$X^1$—$X^2$—$X^3$—$X^4$— and the various subgroups thereof, may be formed by techniques well known in the art and by analogy to the examples provided herein as well. It will also be appreciated that amino acids provide convenient building blocks from which to create the various functionalities which comprise the linking group —$X^1$—$X^2$—$X^3$—$X^4$—. The amino acids used herein include the twenty naturally occurring L-amino acids and their D-enantiomers as well as their derivatives. Amino acid derivatives include compounds such as norvaline, sarcosine, hydroxyproline, N-methyl-L-leucine, aminoisobutyric acid, statine, γ-carboxyglutamic acid, serine-O-phosphate, tyrosine-O-phosphate, tyrosine-O-sulfate, pyroglutamic acid and 4-(E)-butenyl-(R)-methyl-N-methyl-L-threonine. Other amino acid derivatives include the natural L- and unnatural D-amino acids in which side chain functionality is derivatized or protected with common protecting groups, e.g., tert-butoxycarbonyl (BOC). Numerous additional unnatural amino acids are well known and are available from commercial sources, e.g., Aldrich Chemical Co., Milwaukee, Wis. or Sigma Chemical Co., St. Louis, Mo. These materials include β-alanine and higher alkyl chain homologs, 1-amino-1-cyclopropanecarboxylic acid and higher alicyclic ring homologs, 2-amino-2-norbornenecarboxylic acid and isonipecotic acid. The techniques and methods used to synthesize, purify, and evaluate such compounds are well known in the art and are described, e.g., in Synthetic Peptides: A Practical Approach, Atherton, et al., Eds. (IRL Press 1989), which is incorporated herein by reference.

Those of skill in the art will appreciate that compounds of the present invention may be derived from several alternative synthetic strategies. For example, reaction of N-tert-butoxycarbonyl-4-aminobenzyl isocyanate or N,N'-bis-tertbutoxycarbonyl-4-guanidinobenzyl isocyanate with an appropriate mono-protected diaminoalkylene or aminoalkanol provides a suitable intermediate which can be used to prepare compounds of the invention by methods analogous to those described above.

Those of skill in the art will also appreciate that the compounds of the present invention may be derived from other compounds of the invention using well-known chemical transformations.

Those of skill in the art will also appreciate that the compounds of the invention can be converted into the prodrug derivatives thereof. Suitable prodrugs can be represented by the formula $(T-X^1-X^2-X^3-X^4-X^5)_2Y$ in which each $X^1$, $X^2$, $X^3$, $X^4$ and $X^5$ are as defined in the Summary of the Invention and T is —NHR$^4$, —C(NHR$^4$)(NR$^4$) or —NHC(NHR$^4$)(NHR$^4$), wherein $R^4$ is —C(O)OCH(R$^5$)OC(O)R$^6$ and $R^5$ and $R^6$ independently ($C_{1-10}$) alkyl or cyclo($C_{3-10}$)alkyl. Similarly, suitable prodrugs are represented by the formula $R^7-Y-R^8$ in which $R^7$ and $R^8$ are independently $T-X^1-X^2-X^3-X^4-X^5-$ in which T, $X^1$, $X^2$, $X^3$, $X^4$ and $X^5$ are as defined above, with the proviso that $R^7$ and $R^8$ are not the same. Prodrugs of the compounds of the invention can be prepared by methods known to those of ordinary skill in the art (see Saulnier et al., *Bioorganic and Medicinal Chemistry Letters*. 4:1985 (1994)). For example, appropriate prodrugs can be prepared by reacting a non-derivatized compound of the invention with a suitable carbamylating agent (e.g., 1, 1-acyloxyalkylcarbonochloridate, para-nitrophenyl carbonate and the like).

Compounds of this invention can, depending on the nature of their functional groups, form addition salts with various inorganic and organic acids and bases. Typical inorganic acids include, e.g., hydrochloric acid, hydrobromic acid, sulfuric acid, nitric acid, phosphoric acid and the like. Typical organic acids include, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts can also be formed from a carboxylic acid residue by treatment with alkali metals or alkali metal bases, such as alkali metal hydroxides and alkali metal alkoxides, or alkaline earth metals or alkaline earth metal bases, such as alkaline earth metal hydroxides and alkaline earth metal alkoxides. In addition, salts can be formed from a carboxylic acid and an organic base, such as trimethylamine, diethylamine, ethanolamine, piperidine, isopropylamine, choline, caffeine, and the like.

The salts can be formed by conventional means, as by reacting the free acid or base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.

III. In Vitro and In Vivo Testing

In vitro protocols for screening potential inhibitors as to their ability to inhibit tryptase are known in the art. See, e.g., Sturzebecher et al. (1992) *Biol. Chem. Hoppe-Seyler* 373:1025–1030. Typically, these assays measure the tryptase-induced hydrolysis of peptide-based chromogenic substances. Details of an exemplary procedure are described below.

In addition, the activity of the compounds of the present invention can be evaluated in vivo in one of the numerous animal models of asthma. See Larson, "Experimental Models of Reversible Airway Obstruction", in THE LUNG: SCIENTIFIC FOUNDATIONS, Crystal, West et al., eds., Raven Press, New York, 1991; Warner et al. (1990) *Am. Rev. Respir. Dis.* 141:253–257. An ideal animal model would duplicate the chief clinical and physiological features of human asthma, including: airway hyperresponsiveness to chemical mediators and physical stimuli; reversal of airway obstruction by drugs useful in human asthma (β-adrenergics, methyxanthenes, corticosteroids, and the like); airway inflammation with infiltration of activated leukocytes; and chronic inflammatory degenerative changes, such as basement membrane thickening, smooth muscle hypertrophy, and epithelial damage. species used as animal models include mice, rats, guinea pigs, rabbits, dogs, and sheep. All have some limitations, and the proper choice of animal model-depends upon the question which is to be addressed.

The initial asthmatic response can be evaluated in guinea pigs, and dogs, and particularly, with a basenji-greyhound cross strain which develops nonspecific airway hyperresponsiveness to numerous nonallergenic substances, such as methacholine and citric acid. Certain selected sheep exhibit a dual response after antigen challenge with Ascaris proteins. In dual responding animals, the initial asthmatic response (IAR) is followed by a late asthmatic response (LAR) at 6–8 hours post-exposure. Hypersensitivity to the cholinergic agonist carbachol increases at 24 hours after antigen challenge in those animals which exhibit LAR.

The allergic sheep model (see below) was used to evaluate the potential antiasthmatic effects of the compounds of the present invention. Administration of compositions comprising the compounds of the present invention to allergic sheep in both oral and inhalant or aerosol formulations, prior to or following exposure to specific allergens demonstrates that such compositions substantially lessen or abolish the late asthmatic response and consequent hyperresponsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, conjunctivitis, rheumatoid spondylitis, osteoarthritis, gouty arthritis and other arthritic conditions, inflammatory bowel disease, peptic ulcers and various skin conditions. Further, the compounds of the present invention can be used to treat syncytial viral infections.

The efficacy of the compounds of the present invention for the treatment of the vast majority of immunomediated inflammatory disorders can be evaluated by either in vitro or in vivo procedures. Thus, the anti-inflammatory efficacy of the compounds of the present invention can be demonstrated by assays well known in the art, for example, the Reversed Passive Arthus Reaction (RPAR)-PAW technique (see, e.g., Gangly et al. (1992) U.S. Pat. No. 5,126,352). Assays for determining the therapeutic value of compounds in the treatment of various skin conditions, such as hyperproliferative skin disease, are well known in the art, for example, the Arachidonic Acid Mouse Ear Test. The compounds of the present invention can be evaluated for their antiulcer activity according to the procedures described in Chiu et al. (1984)

*Archives Internationales de Pharmacodynamie et de Therapie* 270:128–140.

The efficacy of the compounds of the present invention in blocking cell fusion caused by a syncytial virus infection can be evaluated by the methods generally set forth in Tidwell, et al., *J. Med. Chem.* 26:294–298 (1983).

IV. In Vivo Administration

According to this invention, a therapeutically or pharmaceutically effective amount of a compound of the invention is administered to a patient suffering from an immunomediated inflammatory disorder. According to one embodiment, the compositions of the present invention are useful for preventing or ameliorating asthma. In using the compositions of the present invention in a treatment of asthma, the compounds may be administered prophylactically prior to exposure to allergen or other precipitating factor, or after such exposure. The compounds of the present invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like. In still a further embodiment, the compounds of the present invention are used to treat syncytial viral infections, particularly infections of respiratory syncytial virus.

The compositions containing the compounds can be administered for therapeutic and/or prophylactic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity and course of the disease, previous therapy, the patient's health status and response to the drugs, and the judgment of the treating physician.

In prophylactic applications, compositions containing the compounds of the invention are administered to a patient susceptible to or otherwise at risk of a particular disease in an amount sufficient to prevent or ameliorate the onset of symptoms. Such an amount is defined to be a "prophylactically effective amount or dose." These can be administered orally or by inhalation. In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form.

The composition used in these therapies can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal, topical and parenteral applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES and THE MERCK INDEX $11^{th}$ Ed., (Merck & Co. 1989).

While it is possible to administer the active ingredient of this invention alone, it is preferable to present it as part of a pharmaceutical formulation. The formulations of the present invention comprise at least one compound described herein in a therapeutically or pharmaceutically effective dose together with a pharmacologically acceptable carrier. The pharmaceutical compositions will thus contain the compounds of the present invention in concentrations sufficient to deliver an appropriate dose. For example, where the appropriate dose is 0.05 mg per day, the concentration of the compound of the invention in the pharmaceutical composition would be 0.5 mg per dose, where one dose per day is used. For inhalant or aerosol compositions, the concentration of the compounds of the present invention in the composition will generally depend upon the amount of the dose. Typical concentrations of the compounds of the present invention in inhalant or aerosol compositions would be from about 0.01 to about 30 mg/mL. The formulation may include other clinically useful compounds, such as $\beta$-adrenergics (e.g., albuterol, terbutaline, formoterol, fenoterol, and prenaline) and corticosteroids (e.g., beclomethasome, triamcinolone, flurisolide, and dexamethasone).

EXAMPLES

The following examples are provided merely for the purposes of illustration and are not to be construed in any way as limiting the scope of the present invention.

General Materials and Methods

The compounds described herein may be formed using techniques which are well known in the art, such as those techniques described in March, ADVANCED ORGANIC CHEMISTRY (Wiley 1992); Larock, COMPREHENSIVE ORGANIC TRANSFORMATIONS (VCH 1989); and Furniss, et al., VOGEL'S TEXTBOOK OF PRACTICAL ORGANIC CHEMISTRY 5th ed. (Longman 1989), each of which is incorporated herein by reference. It will be appreciated that the syntheses described herein may require one or more protection and deprotection steps. Accordingly, the use of appropriate protecting groups is necessarily implied by the processes contained herein, although not expressly illustrated. Such protection and deprotection steps may be accomplished by standard methods in addition to those described herein, such as those described in Green and Wuts, PROTECTIVE GROUPS IN ORGANIC SYNTHESIS (Wiley 1991), which is incorporated herein by reference.

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography (HPLC), or a combination of these procedures. Specific illustrations of suitable separation and isolation procedures can be had by reference to the examples hereinafter. However, other equivalent separation or isolation procedures can, of course, be used.

Nuclear magnetic resonance (NMR) spectra were recorded on a General Electric "QE Plus" spectrometer (300 MHz). Infrared (IR) spectra were recorded on a Perkin-Elmer 1600 Fourier Transform IR (FTIR). Analytical HPLC was performed on a Ultrafast Microprotein Analyzer, Michrom BioResources, Inc. equipped with a PLRP or $C_{18}$ column, 1 mm×150 mm. Preparative HPLC was performed on a Gilson LC using a VYDAC 1×25 cm $C_{18}$ reverse phase (RP) column or a Waters Prep LC2000 system using a Vydac 5×25 cm $C_{18}$ RP column. Mass spectra (MS) were obtained on a Finnigan SSQ 710 with an ESI source by direct infusion or by HPLC MS (Ultrafast Microprotein Analyzer, $C_{18}$ column 2 mm×150 mm).

Unless otherwise noted, all reagents and equipment were either prepared according to published procedures or were purchased from commercial sources, such as Aldrich Chemical Co. (Milwaukee, Wis.), Sigma Chemical Co. (St. Louis, Mo.) and ICN Chemical Co. (Irvine, Calif.). The techniques used to perform the syntheses described below will be recognized by those of skill in the art as routine (see, e.g., March, Larock, or Furniss supra).

The following non-limiting Examples are intended to illustrate the present invention. Those skilled in the art will recognize that certain variations and modifications can be practiced within the scope of the invention.

Example 1
trans-1,4-Cyclohexylenedimethylene bis(4-guanidinobenzylcarbamoylmethylaminocarboxylate) (Compound 1)

The following example describes the preparation of a compound of the invention in which Z is guanidino, $X^1$ is $X^6$-$X^7$—$X^8$, wherein n6 is 0, n8 is 1 and $X^7$ is 1,4-phenylene, $X^2$ is NHC(O)—, $X^3$ is methylene, $X^4$ is —NHC(O)O— and Y is trans-1,4cyclohexylenedimethylene.

trans-1,4-Cyclohexylenedimethylene bis(ethoxycarbonylmethylaminocarboxylate)

To a solution of trans-1,4-cyclohexanedimethanol (482 mg, 3.34 mmol.) in DMF (5 mL) was added copper (I) chloride (99 mg, 1.0 mmol.) followed by ethyl isocyanatoacetate (800 μL, 7.13 mmol.) and the resulting suspension was allowed to stir at room temperature over twelve hours. Water (25 mL) and dichloromethane (25 mL) were added to the mixture and the aqueous phase extracted with additional dichloromethane (25 mL). The combined organic layers were washed with water (2×25 mL) followed by saturated aqueous sodium chloride and dried over anhydrous magnesium sulfate. Filtration followed by concentration and drying in vacuo gave trans-1,4-cyclohexylenedimethylene bis [(glycine ethyl ester)-(N)-(α)-carboxylate] (1.19 g, 89%) as a colorless solid.

$^1$H-NMR (300 MHz, CDCl$_3$): 7.42 (tr, 2H), 4.15 (q, 4H), 3.75 (d, 4H), 3.70 (d, 4H), 1.80–1.60 (m, 4H), 1.55–1.40 (m, 2H), 1.15 (tr, 6H), 1.00–0.80 (m, 4H).

trans-1,4-Cyclohexylenedimethylene bis(ethoxycarbonylmethyl aminocarboxylate)

To a solution of trans-1,4-cyclohexylene bis(N-methoxycarbonylglycine) (1.19 g, 2.96 mmol.) in tetrahydrofuran:methanol 3:1 (25 mL) was added aqueous sodium hydroxide (1.6M, 6 mL, 9.7 mmol.) and the mixture was allowed to stir at room temperature over twelve hours. Concentration followed by acidification of the aqueous solution to pH=1 by dropwise addition of concentrated aqueous hydrochloric acid gave a white precipitate. Filtration and drying in vacuo gave trans-1,4-cyclohexylene bis (N-methoxycarbonylglycine) as a colorless solid.

$^1$H-NMR (300 MHz, DMSO-d$_6$): 12.50 (s, 2H), 7.30 (tr, 2H), 3.75 (d, 4H), 3.60 (d, 4H), 1.80–1.60 (m, 4H), 1.55–1.50 (m, 2H), 1.00–0.80 (m, 4H).

trans-1,4-Cyclohexylenedimethylene bis(4-aminobenzylcarbamoylmethylaminocarboxylate)

trans-1,4-Cyclohexylene bis(N-methoxycarbonylglycine) (306 mg, 0.88 mmol.), hydroxybenztriazole hydrate (260 mg, 1.92 mmol.), and 1-(3-dimethylaminopropyl)-3-ethylcarbodiimide hydrochloride (360 mg, 1.88 mmol.) were dissolved in DMF (5 mL) at 0° C. and the resulting solution allowed to stir for one hour. 4-Aminobenzylamine (300 μL, 2.64 mmol.) was then added to the mixture which was subsequently allowed to warm to room temperature and stirred an additional twelve hours. Removal of DMF in vacuo followed by addition of water (25 mL), filtration of the insoluble residue and drying in vacuo gave the desired aniline as a tan solid.

$^1$H-NMR (300 MHz, DMSO-d$_6$): 8.10 (tr, 2H), 7.20 (tr, 2H), 6.90 (d, 4H), 6.50 (d, 4H), 5.40 (br s, 2H), 4.05 (d, 4H), 3.75 (d, 4H), 3.55 (d, 4H), 1.80–1.60 (m, 4H), 1.50–1.40 (m, 2H), 1.00–0.80 (m, 4H).

trans-1,4-Cyclohexylenedimethylene bis(4-quanidinobenzylcarbamoylmethylaminocarboxylate) (Compound 1)

trans-1,4-Cyclohexylenedimethylene bis(4-aminobenzylcarbamoylmethylaminocarboxylate) (87 mg, 0.16 mmol.) and cyanamide (0.5 g, 11.9 mmol.) were heated neat at 60° C. to give a colorless solution followed by addition of hydrogen chloride (4M in dioxane, 160 μL, 0.64 mmol.). The resulting yellow liquid was stirred at 60° C. an additional 1.5 hours followed by cooling to room temperature. Addition of ethyl ether (25 mL) gave an insoluble yellow oil which was repeatedly washed with additional ethyl ether (3×25 mL) to remove residual cyanamide followed by drying in vacuo. The yellow oil was then taken into water (5 mL) and purified by preparative reverse phase HPLC to give trans-1,4-cyclohexylenedimethylene bis(4-guanidinobenzylcarbamoylmethylaminocarboxylate (Compound 1) bis-trifluoroacetate as a colorless solid.

$^1$H-NMR (300 MHZ, DMSO-d$_6$): 9.80 (s, 2H), 8.40 (tr, 2H), 7.20 (tr, 2H), 7.40 (s, 8H), 7.30 (d, 4H), 7.10 (d, 4H), 4.25 (d, 4H), 3.75 (d, 4H), 3.60 (d, 4H), 1.80–1.60 (m, 4H), 1.55–1.40 (m, 2H), 1.00–0.85 (m, 4H).

Electrospray LRMS: Calculated for $C_{30}H_{42}N_{10}O_6$: MH$^+$: 639.7; MH$_2^{+2}$/2: 320.4 Found: MH$^+$: 639.1; MH$_2^{+2}$/2: 319.8.

Proceeding in a fashion analogous to the procedure described in Example 1 and substituting different starting materials the following compounds of the invention were prepared:

cis-1,5-cyclooctylene bis{4-[3-(1-amidinopiperid-4-yl) propionoyl]-1-piperazinecarboxylate} (Compound 5); Electrospray LRMS: Calculated for $C_{36}H_{64}N_8O_6$: MH$^+$: 731; Found: MH$^+$: 730.7;

cis-1,5-cyclooctylene bis {4-[3(4-amidinophenyl) propionoyl]-1-piperazinecarboxylate} (Compound 6); Electrospray LRMS: Calculated for $C_{38}H_{52}N_8O_6$:MH$^+$: 716.9; Found: MH$^+$: 717.9; and cis-1,5-cyclooctylene bis{[4-(1-amidinopiperid-4-ylacetyl)-1-piperazinecarboxylate]} (Compound 7); $^1$H-NMR (300 MHz, DMSO-d$_6$): 7.2(m, 8H), 4.6(s, 2H), 3.8(d, 8H), 3.4(m, 16H), 2.9(t, 4H), 2.3(s, 4H), 1.9(m, 2H), 1.6(m, 10H), 1.1(m, 4H).

Example 2 cis-1,5-Cyclooctylene bis[(N-(4-guanidinobenzylcarbamoylmethyl aminocarboxylate) (Compound 2)

The following example describes the preparation of a compound of the invention in which Z is guanidino, $X^1$ is $X^6$—$X^7$—$X^8$, wherein n6 is 0, n8 is 1 and $X^7$ is 1,4-phenylene, $X^2$ is —NHC(O)—, $X^3$ is methylene, $X^4$ is —NHC(O)O— and Y is cis-1,5-cyclooctylene. cis-1,5-cyclooctylene.

cis-1,5-Cyclooctylene bis(ethoxycarbonylmethylaminocarboxylate)

To a solution of cis-1,5-cyclooctanediol (514 mg, 3.56 mmol.) in DMF (5 mL) was added copper (I) chloride (110 mg, 1.1 mmol.) followed by ethyl isocyanatoacetate (850 μL, 7.6 mmol.) and the resulting suspension was allowed to stir at room temperature over twelve hours. Water (25 mL) and dichloromethane (25 mL) were added to the mixture and the aqueous phase extracted with additional dichloromethane (25 mL). The combined organic layers were washed with water (2×25 mL) followed by saturated aqueous sodium chloride and dried over anhydrous magnesium sulfate. Filtration followed by concentration and drying in vacuo gave cis-1,5-cyclooctylene bis(ethoxycarbonylmethylaminocarboxylate) as a colorless oil.
$^1$H-NMR (300 MHZ, DMSO-$d_6$): 7.40 (tr, 2H), 4.60 (m, 2H), 4.05 (q, 4H), 3.65 (d, 4H), 1.80–1.40 (m, 12H), 1.15 (tr, 6H).

Cis-1,5-Cyclooctylene bis(N-methoxycarbonylglycine)

To a solution of cis-1,5-cyclooctylene bis(ethoxycarbonylmethylaminocarboxylate) (1.26 g, 3.1 mmol.) in tetrahydrofuran:methanol 3:1 (25 mL) was added aqueous sodium hydroxide (1.6M, 6 mL, 9.4 mmol.) and the mixture was allowed to stir at room temperature over twelve hours. Concentration followed by acidification of the aqueous solution to pH=1 by dropwise addition of concentrated aqueous hydrochloric acid and extraction of the aqueous solution with ethyl acetate (3×25 mL) gave the crude diacid. Drying the combined organic layers over anhydrous magnesium sulfate followed by filtration and concentration in vacuo gave cis-1,5-cyclooctylene bis(N-methoxycarbonylglycine) as a colorless oil.
$^1$H-NMR (300 MHz, DMSO-$d_6$): 7.25 (tr, 2H), 4.60 (m, 2H), 3.60 (d, 4H), 1.80–1.40 (m, 12H).

cis-1,5-Cyclooctylene bis(4-guanidinobenzylcarbamoylmethylaminocarboxylate) (Compound 2)

cis-1,5-Cyclooctylene bis(N-methoxycarbonylglycine) (64 mg, 0.19 mmol.) in dimethylformamide (3 mL) was cooled to 0° C. and hydroxybenztriazole (61 mg, 0.45 mmol.) was added followed by 1-(3-dimethylaminopropyl)-3-ethylcarbodiimide hydrochloride (76 mg, 0.40 mmol.). The resulting mixture was stirred at 0° C. over one hour then added by cannula to a slurry containing 4-guanidinophenylmethylamine bis-trifluoroacetate (290 mg, 0.74 mmol.) and triethylamine (500 μL, 3.6 mmol.) in dimethylformamide (2 mL) cooled to 0° C. The mixture was then allowed to slowly warm to room temperature over twelve hours followed by concentration in vacuo. The residue was taken into water (10 mL) and the solution pH adjusted to 11–12 by dropwise addition of saturated aqueous sodium carbonate. The insoluble product was collected by decantation of the aqueous solution and the crude material taken back into aqueous solution by acidification to pH=1–2 with concentrated aqueous hydrochloric acid. The material was then purified by preparative reverse phase HPLC to give cis-1,5-cyclooctylene bis(4-guanidinobenzylcarbamoylmethylaminocarboxylate) (Compound 2) bis-trifluoroacetate as a colorless solid.
$^1$H-NMR (300 MHz, DMSO-$d_6$): 9.80 (s, 2H), 8.40 (tr, 2H), 7.40 (s, 8H), 7.25 (d, 4H), 7.20 (tr, 2H), 7.10 (d, 4H), 4.60 (m, 2H), 4.25 (d, 4H), 3.60 (d, 4H), 1.80–1.40 (m, 12H).
Electrospray LRMS: Calculated for $C_{30}H_{42}N_{10}O_6$: MH$^+$: 639.7; MH$_2^{+2}$/2: 320.4 Found: MH$^+$: 639.1; MH$_2^{+2}$/2: 319.8

4-Guanidinobenzylamine bis-triflouroacetate

4-Aminobenzylamine (11.0 g, 90 mmol.) in dichloromethane (30 mL) was cooled to 0° C. and di-tert-butyl dicarbonate (18.65 g, 85 mmol.) was added to the solution and the mixture was allowed to slowly warm to room temperature over twelve hours. Subsequent filtration followed by washing the dichloromethane solution with saturated aqueous ammonium chloride then with saturated aqueous sodium chloride, drying over anhydrous magnesium sulfate, filtration and concentration gave 4-amino-N-tert-butoxycarbonylbenzylamine as a yellow oil. A methanol solution of the aniline was acidified with hydrogen chloride in dioxane (one equivalent) and the hydrochloride salt crystallized by addition of ethyl ether to the acidic solution. Filtration and drying in vacuo provided the hydrochloride salt as a yellow crystalline solid which was guanylated without further purification.

4-Amino-N-tert-butoxycarbonylbenzylamine hydrochloride (25.77 g, 99.6 mmol.) and cyanamide (55 g, 1.3 mol.) were heated neat at 65° C. over 1.5 hours. The mixture was then cooled to room temperature and ether (250 mL) was added. The insoluble yellow oil was repeatedly washed with additional ethyl ether to remove traces of cyanamide and dried in vacuo to give 4-guanidino-N-tert-butoxycarbonylbenzylamine hydrochloride as an amorphous yellow material which was carried on without further purification.

4-Guanidino-N-tert-butoxycarbonylbenzylamine hydrochloride (14.4 g, 48 mmol.) was taken up into trifluoroacetic acid (35 mL) and the resulting yellow solution stirred over 30 minutes. Concentration and drying in vacuo gave 4-guanidinobenzylamine bis-trifluoroacetate as a yellow oil.
$^1$H-NMR (300 KHz, DMSO-$d_6$): 10.25 (s, 1H), 8.40 (br s, 3H), 7.65 (br s, 4H), 7.50 (d, 2H), 7.25 (d, 2H), 4.00 (d, 2H).

Example 3 cis-1,5-Cyclooctylene bis[4-(4-guanidinobenzylcarbamayl)-1-piperazinecarboxylate] (Compound 3)

The following example describes the preparation of a compound of the invention in which Z is guanidino, $X^1$ is $X^6$—$X^7$–$X^8$—, wherein n6 is 0, n8 is 1 and $X^7$ is 1,4-phenylene, $X^2$ is —NHC(O)—, $X^3$ is 1,4-piperazinylene, $X^4$ is —C(O)O— and Y is cis-1,5-cyclooctylene.

Method A

Cis-1,5-Cyclooctanediol bis-chloroformate

Cis-1,5-Cyclooctanediol (3.05 g, 21.2 mmol.) was added to a solution of phosgene in toluene (1.9M, 28.0 mL, 53 mmol.) and the mixture was cooled to 0° C. under a nitrogen atmosphere. Pyridine (3.4 mL, 43 mmol.) was subsequently added by syringe and the resulting suspension was allowed to warm to room temperature over twelve hours. Dichloromethane (50 mL) and water (50 mL) were added to the reaction mixture and the organic layer washed with 0.1 N aqueous hydrochloric acid (2×25 mL). The dichloromethane solution was then dried over anhydrous magnesium sulfate, filtered and concentrated in vacuo to give the crude chloroformate (3.7 g, 65% yield) as a yellow crystalline solid. Further purification by silica gel flash chromatography using ethyl ether:hexanes 1:10 gives the pure chloroformate as a colorless crystalline solid.

¹H-NMR (300 MHz, CDCl₃): 5.00–4.85 (m, 2H), 2.20–1.60 (m, 12H).

cis-1,5-Cyclooctylene bis(4-(tert-butoxycarbonyl)-1-piperazinecarboxylate]

cis-1,5-Cyclooctanediol bis-chloroformate (3.69 g, 13.7 mmol.) and diisopropylethylamine (7.2 mL, 41 mmol.) were taken into DMF (25 mL) followed by addition of tert-butyl 1-piperazinecarboxylate (5.1 g, 27.4 mmol.) and the mixture was allowed to stir at room temperature twelve hours. Concentration in vacuo to a semi-solid residue and addition of dichloromethane (50 mL) and water (50 mL) followed by washing the organic layer with 0.1N aqueous hydrochloric acid (2×25 mL) gave a crude solution of the desired carbamate. The dichloromethane solution was then dried over anhydrous magnesium sulfate, filtered and concentrated in vacuo to give cis-1,5-cyclooctylene bis[4-(tert-butoxycarbonyl)-1-piperazinecarboxylate] as an amorphous solid which was employed without further purification.

¹H-NMR (300 MHz, CDCl₃): 4.80 (m, 2H), 3.40 (br s, 16H), 2.00–1.40 (m, 12H), 1.40 (s, 18H).

cis-1,5-Cyclooctylene bis(1-piperazinecarboxylate) bis-hydrochloride cis-1,5-Cyclooctylene bis[4-(tert-butoxycarbonyl)-1-piperazinecarboxylate] as obtained by the above procedure was treated with trifluoroacetic acid (15 mL) at room temperature for fifteen minutes followed by concentration in vacuo. The resulting oil was taken into water (30 mL) and basified with an excess of solid potassium carbonate. The diamine was then extracted with dichloromethane (3×25 mL) and the combined organic layers dried over anhydrous magnesium sulfate. Filtration followed by concentration provided cis-1,5-cyclooctylene bis(1-piperazinecarboxylate) as a colorless oil. The diamine was then taken up into methanol (15 mL) and treated with hydrogen chloride in dioxane solution (4.0M, 5.3 mL) followed by addition of ethyl ether (250 mL). The precipitate was collected by filtration and washed with additional ethyl ether followed by drying in vacuo to afford cis-1,5-cyclooctylene bis(1-piperazinecarboxylate) bis-hydrochloride as a colorless solid.

¹H-NMR (300 MHz, DMSO-d₆): 9.50 (br s, 4H), 4.65 (m, 2H), 3.60 (s, 8H), 3.05 (s, 8H) 1.90–1.40 (m, 12H).

cis-1,5-Cyclooctylene bis[4-((p-tertbutoxycarbonylaminobenzyl)carbamoyl)-1-piperazinecarboxylate]

cis-1,5-Cyclooctylene bis(1-piperazinecarboxylate) bis-hydrochloride (1.94 g, 4.5 mmol.) was taken into dichloromethane (75 mL) followed by addition of diisopropylethylamine (2.0 mL, 11.5 mmol.). 4-Aminophenylmethyl isocyanate tert-butylcarbamate (2.26 g, 9.1 mmol.) was subsequently added and the mixture was allowed to stir for two hours at room temperature. The dichloromethane solution was washed with 0.5N aqueous hydrochloric acid (2×50 mL) followed by drying over anhydrous magnesium sulfate and filtration. Concentration in vacuo followed by silica gel flash chromatography with ethyl ether followed by ethyl acetate:ethanol 10:1 eluent afforded pure cis-1,5-cyclooctylene bis[4-((p-tert-butoxycarbonylaminobenzyl)carbamoyl)-1-piperazinecarboxylate] (3.5 g, 90% yield) as a colorless foam.

¹H-NMR (300 MHz, CDCl₃): 7.25 (dd AB, 8H), 6.70 (s, 2H), 5.00 (tr, 2H), 4.80 (m, 2H), 4.30 (d, 4H), 3.45–3.30 (m, 16H), 2.00–1.40 (m, 12H), 1.50 (s, 18H).

cis-1,5-Cyclooctylene bis[4-((p-aminobenzyl)carbamoyl)-1-piperazinecarboxylate]

cis-1,5-Cyclooctylene bis[4-((p-tertbutoxycarbonylaminobenzyl)carbamoyl)-1-piperazinecarboxylate] (3.5 g, 4.0 mmol.) was treated with hydrogen chloride in dioxane (4.0M, 20 mL) for 30 minutes at room temperature followed by dilution with ethyl ether (100 mL). The solvent was carefully decanted away from the hydrochloride salt precipitate and dried in vacuo to give cis-1,5-cyclooctylene bis[4-((p-aminobenzyl)carbamoyl)-1-piperazinecarboxylate]bis-hydrochloride as a hygroscopic tan solid which was employed without further purification.

¹H-NMR (300 MHz, DMSO-d₆): 10.25 (br s, 6H), 7.30 (dd AB, 8H), 7.15 (tr, 2H), 4.60 (m, 2H), 4.20 (d, 4H), 3.30 (s, 16H), 1.80–1.40 (m, 12H).

cis-1,5-Cyclooctylene bis[4-((4-guanidinobenzyl)carbamoyl)-1-piperazinecarboxylate] (Compound 3)

cis-1,5-Cyclooctylene bis[4-((p-aminobenzyl)carbamoyl)-1-piperazinecarboxylate]bis-hydrochloride as obtained by the above procedure was heated neat with excess cyanamide (8.0 g, 190 mmol.) at 60–65° C. for 1.5 hours. The resulting yellow solution was cooled to room temperature and ethyl ether (250 mL) was added. The insoluble residue was washed with additional ethyl ether (3×100 mL) and the crude hydrochloride salt dried in vacuo. The amorphous material was then taken into water (40 mL) and the suspension filtered using Millipore filter paper type GV (0.22 μm). The resulting aqueous filtrate was purified by preparative reverse phase HPLC followed by lyophilization to afford cis-1,5-cyclooctylene bis[4-((4-guanidinobenzyl)carbamoyl)-1-piperazinecarboxylate] (Compound 3) bis-hydrochloride as an off white solid.

¹H-NMR (300 MHz, DMSO-d₆): 9.70 (s, 2H), 7.40 (s, 8H), 7.20 (dd AB, 8H), 7.15 (tr, 2H), 4.65 (m, 2H), 4.20 (d, 4H), 3.30 (s, 16H), 1.80–1.40 (m, 12H).

Electrospray LRMS: Calculated for $C_{36}H_{52}N_{12}O_6$: MH⁺: 749.9; $MH_2^{+2}/2$: 375.5 Found: MH⁺: 749.9; $MH_2^{+2}/2$: 375.3

4-(tert-Butoxycarbonylamino)benzylamine hydrochloride

4-Aminobenzylamine (5.56 g, 45.6 mmol.) was taken up into water (45 mL) and citric acid (9.63 g, 50 mmol.) was added to the solution. Di-tert-butyl dicarbonate (9.94 g, 45.5 mmol.) in dioxane (20 mL) was added dropwise to the above solution and the mixture was allowed to stir at room temperature over 48 hours. The yellow suspension was then filtered and the aqueous solution basified with excess solid sodium carbonate. Extraction of the aqueous solution with ethyl acetate (3×35 mL) followed by washing the combined organic layers with saturated aqueous sodium chloride and drying over anhydrous sodium sulfate afforded the crude benzylamine. Filtration and concentration in vacuo gave a white solid which was taken into methanol (30 mL) and acidified with hydrogen chloride in dioxane (4M, 8.4 mL, 33.6 mmol.). Addition of ethyl ether (100 mL) followed by filtration of the resulting suspension and drying in vacuo provided 4-(tert-butoxycarbonylamino)benzylamine hydrochloride (7.2 g, 61% yield) as a colorless solid.

¹H-NMR (300 MHz, DMSO-d₆): 9.43 (s, 1H), 8.20 (br s, 3H), 7.40 (dd AB, 4H), 3.92 (m, 2H), 1.50 (s, 9H).

(tert-Butoxycarbonylamino)benzyl isocyanate 4-(tert-Butoxycarbonylamino)benzylamine hydrochloride (3.39 g, 13.1 mmol.) was taken up into dichloromethane (120 mL) at 0° C. followed by addition of pyridine (4.3 mL, 53 mmol.) and triphosgene (1.3 g, 4.4 mmol.). The mixture was allowed to slowly warm to room temperature over twelve hours followed by addition of aqueous hydrochloric acid (0.5N, 100 mL). The organic layer was dried over anhydrous magnesium sulfate and filtered followed by concentration to afford (tert-Butoxycarbonylamino)benzyl isocyanate (2.7 g, 84% yield) as a brown solid.

¹H-NMR (300 MHz, CDCl₃): 7.29 (dd AB, 4H), 6.55 (br s, 1H), 4.40 (s, 2H), 1.55 (s, 9H).

Method B tert-Butyl 1-piperazinecarboxylate-4-carbonyl chloride tert-Butyl 1-piperazinecarboxylate (321 mg, 1.72 mmol.) was taken up into dichloromethane (3.0 mL) followed by addition of pyridine (210 µL, 2.6 mmol.) and the resulting solution cooled to 0° C. Triphosgene (255 mg, 0.86 mmol.) was subsequently added and the reaction mixture was allowed to warm to room temperature over 30 minutes. Aqueous hydrochloric acid (0.1N, 5.0 mL) and dichloromethane (5 mL) were added to the mixture and the organic layer was dried over anhydrous magnesium sulfate. Filtration and concentration in vacuo gave tert-butyl 1-piperazinecarboxylate-4-carbonyl chloride (416 mg, 97%) as a yellow crystalline solid.

¹H-NMR (300 MHz, CDCl₃): 3.70 (m, 2H), 3.60 (m, 2H), 3.50 (m, 4H), 1.50 (s, 9H).

1-[(4-Guanidinobenzyl)carbamoyl]piperazine bis-trifloroacetate

4-Guanidinobenzylamine bis-trifluoroacetate (380 mg, 0.97 mmol.) was taken up into DMF (2.0 mL) followed by addition of diisopropylethylamine (700 µL, 4.0 mmol.). tert-Butyl 1-piperazinecarboxylate-4-carbamoyl chloride (241 mg, 0.97 mmol.) was subsequently added and the mixture was allowed to stir at room temperature over one hour. The resulting solution was concentrated in vacuo and taken up into water (5 mL). Filtration of the resulting suspension followed by basification of the aqueous solution with excess solid sodium carbonate gave an insoluble yellow oil which was separated from the aqueous phase by decantation. Drying in vacuo followed by treatment with trifluoroacetic acid (5 mL) for fifteen minutes afforded the crude phenylguanidine bis-triflouroacetate as an orange oil upon concentration. The salt was then taken into water (5 mL) and the material purified by preparative reverse phase HPLC and lyophilization to give 1-[(4-Guanidinobenzyl)carbamoyl] piperazine bis-trifloroacetate as a yellow amorphous solid.

¹H-NMR (300 MHz, DMSO-d₆): 10.15 (s, 1H), 9.10 (br s, 2H), 7.65 (s, 4H), 7.40 (tr, 1H), 7.25 (dd AB, 4H), 4.25 (d, 2H), 3.55 (m, 4H), 3.10 (s, 4H).

Electrospray LRMS: Calculated for $C_{13}H_{20}N_6O$: MH⁺: 277.4; $MH2^{+2}/2$: 139.2 Found: MH⁺: 277.4; $MH_2^{+2}/2$: 139.3 cis-1,5-Cyclooctylene bis[4-((4-guanidinobenzyl)carbamoyl)-1-piperazinecarboxylate] (Compound 3)

1-[(4-Guanidinobenzyl)carbamoyl]piperazine bis-trifloroacetate (138 mg, 0.27 mmol.) was taken up into DMF (1.5 mL) followed by addition of diisopropylethylamine (71.5 µL, 0.4 mmol.) and cis-1,5-cyclooctanediol bis-chloroformate (36.0 mg, 0.14 mmol.). The reaction mixture was allowed to stir at room temperature over twelve hours followed by concentration in vacuo. The amorphous residue was taken up into water (5 mL) and the material purified by preparative reverse phase HPLC followed by lyophilization to give cis-1,5-cyclooctylene bis[4((4-guanidinobenzyl) carbamoyl)-1-piperazinecarboxylate] (Compound 3) as an off white solid.

Method C

N-tert-butyl-N'-4-aminobenzylurea hydrochloride

4-Aminobenzylamine (50.34 g, 0.412 mol) in dichloromethane (200 mL) was placed in a one liter 3-neck round bottom flask fitted with mechanical stirring apparatus and the solution cooled to 0° C. di-tert-Butyl dicarbonate (89.9 g, 0.412 mol) in dichloromethane (200 mL) was added dropwise to the solution over 30 minutes and the resulting suspension was allowed to stir at 0° C. an additional two hours at which point a nearly homogeneous solution was obtained. The dichloromethane solution was subsequently washed with aqueous sodium hydroxide (1.0M, 500 mL) followed by water (500 mL) and the organic phase dried over anhydrous magnesium sulfate. Filtration followed by concentration in vacuo gave 4-amino-N-tert-butylcarbomoylbenzylamine as a yellow oil. The aniline was then taken into ethyl ether:methanol (2:1, 225 mL) and the solution cooled to 0° C. Acidification with hydrogen chloride in dioxane (4.0M, 115 mL, 0.412 mol) followed by addition of ethyl ether (200 mL) gave a thick pale yellow precipitate. Filtration followed by washing with additional ethyl ether (500 mL) and drying in vacuo provided N-tert-butyl-N'-4-aminobenzylurea hydrochloride (100.23 g, 94% yield) as a pale yellow solid which was used without further purification.

¹H-NMR (300 MHz, DMSO-d₆): 10.40–10.20 (br s, 3H) 7.40 (tr, 1H), 7.30 (s, 4H), 4.10 (d, 2H), 1.40 (s, 9H).

N-tert-butyl-N-4-guanidinobenzylurea

Cyanamide (100 g, 2.4 mol) was placed in a 500 mL round bottom flask and heated to 60–65° C. until the material completely melted. N-tert-butyl-N'-4-aminobenzylurea hydrochloride, (25.3 g, 97.8 mmol) was then added directly to the liquid cyanamide and the resulting yellow solution was stirred at 60–65° C. an additional two hours. Water (100 mL) was subsequently added to the solution followed by cooling to room temperature. The aqueous solution was washed with ethyl ether (1 L) followed by back extraction of the organic phase with water (2×, 100 mL). The combined aqueous layers were again washed with ethyl ether (500 mL) and the aqueous solution cooled in an ice water bath followed by basification with aqueous sodium hydroxide (10M, 100 mL). The resulting insoluble oil slowly crystalized and was collected by filtration. The material then was washed with water and dried in vacuo to give N-tert-butyl-N-4-guanidinobenzylurea (18.3 g, 70.8%) as a colorless crystalline solid.

¹H-NMR (300 MHz, DMSO-d₆): 9.70 (s, 1H), 7.42 (tr, 1H), 7.40 (s, 4H), 7.25 (d, 2H), 7.15 (d, 2H), 4.10 (d, 2H), 1.40 (s, 9H)

tert-Butyl 4-chlorocarbonyl-1-piperazinecarboxylate

Triphosgene (25 g, 84.2 mmol) was taken into dichloromethane (200 mL) and the resulting solution cooled to 0° C. A solution of tert-butyl 1-piperazinecarboxylate (40 g, 214.8 mmol) and pyridine (35 mL, 432.7 mmol) in dichloromethane (100 mL) was then added dropwise to the triphosgene solution and the reaction mixture was allowed to warm to room temperature over 30 minutes. The mixture was then quenched by addition of aqueous hydrochloric acid (0.1N, 200 mL) and the aqueous phase washed with dichloromethane (50 mL) followed by drying the combined organic layers over anhydrous magnesium sulfate. Filtration and concentration in vacuo gave tert-butyl 4-chlorocarbonyl-1-piperazinecarboxylate (45.6 g, 85%) as a yellow solid which may be used without further purification. The material can be purified further by crystallization from ethyl ether/hexane.

¹H-NMR (300 MHz, CDCl₃: 3.70 (m, 2H), 3.60 (m, 2H), 3.50 (m, 4H), 1.50 (s, 9H).

tert-Butyl 4-guanidinobenzylcarbamoyl-1-piperazinecarboxylate trifluoroacete

N-tert-butyl-N-4-guanidinobenzylurea (41.77 g, 0.158 mol) was treated with trifluoroacetic acid (100 mL) for 30 minutes at room temperature. The resulting nearly colorless liquid was concentrated in vacuo at 45° C. then triturated with ethyl ether (3×400 mL) and dried in vacuo to a colorless foam. Methanol (200 mL) was added to the residue followed by diisopropylethylamine (55 mL, 0.32 mol., amount based on estimated excess TFA present) and the solution was cooled to 0° C. tert-Butyl 1-piperazinecarboxylate-4-carbamoyl chloride (39.3 g, 0.158 mol) in dichloromethane (120 mL) was added to the reaction mixture followed by additional diisopropylethylamine (30 mL). The reaction mixture was allowed to warm to room temperature and stirred for an additional 12 hours. Concentration in vacuo to an orange oil followed by addition of water (200 mL) gave a thick precipitate which was collected by filtration. The crude guanidine TFA salt was recrystallized from acetonitrile/ether to give tert-butyl 4-guanidinobenzylcarbamoyl-1-piperazinecarboxylate trifluoroacete (62.0 g, 80%) as a pale yellow solid.

$^1$H-NMR (300 MHz, DMSO-d$_6$): 10.15 (s, 1H), 9.10 (br s, 2H), 7.65 (s, 4H), 7.40 (tr, 1H), 7.25 (dd AB, 4H), 4.25 (d, 2H), 3.55 (m, 4H), 3.10 (s, 4H).

Electrospray LRMS: Calculated for $C_{13}H_{20}N_6O$: MH$^+$: 277.4; MH$_2^{+2}$/2: 139.2 Found: MH$^+$: 277.4; MH$_2^{+2}$/2: 139.3.

cis-1,5-cyclooctylene bis[4-4-guanidinobenzylaminecarbonyl)-1-piperazinecarboxylate (Compound 3)

tert-Butyl 4-guanidinobenzylcarbamoyl-1-piperazinecarboxylate trifluoroacete (50 g, 0.102 mol) was treated with trifluoroacetic acid (50 mL) at room temperature for 15 minutes to give a homogeneous solution. The bulk of TFA was removed in vacuo giving a water soluble amorphous residue. This material is then taken into water (100 mL) and the pH adjusted to 7.0–7.5 by careful addition of 10M aqueous sodium hydroxide. cis-1,5-cyclooctylene bis-chloroformate (13.5 g, 0.05 mol) in THF (75 mL) is added to the above aqueous solution and the mixture is stirred at room temperature. The pH of this mixture is monitored using a standard laboratory pH meter and continually readjusted to the 7.0–8.0 range by addition of 10M aqueous sodium hydroxide as needed. After the pH is stabilized (approximately one hour) the reaction is determined to be complete by reverse phase analytical HPLC. Ethyl ether (50 mL) is then added to the nearly homogeneous solution followed by basification of the biphasic mixture with an excess of 10M aqueous sodium hydroxide giving a white suspension of free base arylguanidine. This suspension is concentrated on the rotary evaporator to remove the bulk of THF and the fine precipitate collected by filtration. The paste consistency solid then was washed once with water and dried in vacuo to give cis-1,5-cyclooctylene bis[4-4-guanidinobenzylaminecarbonyl)-1-piperazinecarboxylate (31 g, 81%) as a white solid (purity>97% as determined by HPLC). The free base was dissolved in aqueous hydrochloric acid and filtered to remove traces of insoluble residue and lyophilization to give cis-1,5-cyclooctylene bis[4-4-guanidinobenzylaminecarbonyl)-1-piperazinecarboxylate hydrochloride.

$^1$H-NMR (hydrochloride salt) (300 MHz, DMSO-d$_6$): 9.70 (s, 2H), 7.40 (s, 8H), 7.20 (dd AB, 8H), 7.15 (tr, 2H), 4.65 (m, 2H), 4.20 (d, 4H), 3.30 (s, 16H), 1.80–1.40 (m, 12H). Electrospray LRMS (hydrochloride salt): Calculated for $C_{36}H_{52}N_{12}O_6$: MH$^+$: 749.9; MH$_2^{+2}$/2: 375.5 Found: MH$^+$: 749.9; MH$_2^{+2}$/2: 375.3.

Proceeding in a fashion analogous to the procedure described in Example 3, Method A, and substituting different starting materials, the following compounds of the invention were prepared:

cis-1,5-cyclooctylene bis{4-[2-(1-amidinopiperid-4-yl) ethylcarbamoyl]-1-piperazinecarboxylate} (Compound 8); $^1$H-NMR (300 MHz, DMSO-d$_6$): 7.4(s. 8H), 6.6(s, 2H), 4.6(s, 2H), 3.8(d, 4H), 3.6(s, 8H), 3.3(s, 14H), 3.0 (m, 20H) 1.0(m, 4H);

cis-1,5-cyclooctylene bis{4-(trans-4-aminomethylcyclohexylcarbonyl)-1-piperazinecarboxylate] (Compound 9); Electrospray LRMS: Calculated for $C_{38}H_{62}N_6O_6$: MH$^+$: 647.9 Found: MH$^+$648.1;

cis-1,5-cyclooctylene bis [4-(4-guanidinophenylacetyl)-1-piperazinecarboxylate] (Compound 10); Electrospray LRMS: Calculated for $C_{36}H_{50}N_{10}O_6$; MH$^+$; 718.9; Found: MH$^+$: 717.3;

cis-1,5-cyclooctylene bis[4-[3-(4-guanidinophenyl) propionyl]-1-piperazinecarboxylate} (Compound 11); Electrospray LRMS: Calculated for $C_{38}H_{54}N_{10}O_6$; MH$^+$; 746.9; Found: MH$^+$: 745.5;

cis-1,5-cyclooctylene bis [4- (trans-4-aminomethylcyclohexylmethylcarbamoyl)-1-(perhydro-7H-1,4-diazepine)carboxylate] (Compound 12); Electrospray LRMS: Calculated for $C_{38}H_{68}N_8O_6$: MH$^+$: 734; MH$_2^{+2}$/2: 367.5; Found: MH$_2^{+2}$/2: 367.7;

cis-1,5-cyclooctylene bis[4-(4-aminomethylbenzylcarbamoyl)-1-piperazinecarboxylate] (Compound 13); Electrospray LRMS: Calculated for $C_{36}H_{52}N_8O_6$: MH$^+$: 693.9; Found: MH$^+$: 693.5;

cis-1,5-cyclooctylene bis {4-[4-(2-aminoethyl) benzylcarbamoyl]1-piperazinecarboxylate] (Compound 14); $^1$H-NMR (300 MHz, DXSO-d$_6$): 7.34, 7.15(d, 8H), 4.64(bt, 4H), 4.15(m, 2H), 3.92(d, 4H), 3.54(m, 4H), 3.25(appd, 16H), 1.73–1.47(m, 12H); Electrospray LRMS: Calculated for $C_{38}H_{56}N_8O_6$: MH$^+$: 721; Found: MH$^+$: 721;

cis-1,5-cyclooctylene [4-(4-aminomethylbicyclo[2.2.2]oct-1-ylmethylcarbamoyl)-1-piperazinecarboxylate] (Compound 15); $^1$H-MNR (300 MHz, DMSO-d$_6$): 4.18 (m, 2H), 3.40(m, 4H), 3.21(d, 16H), 2.8(d, 4H), 1.75–1.39 (m, 36H);

cis-1,5-cyclooctylene bis{4-[4-(2-aminoethyl) phenylacetyl]-1-piperazinecarboxylate}] (Compound 16); $^1$H-NMR (300 MHz, DMSO-d$_6$): 7.13, 6.93(d, 8H), 5.8(d, 4H), 3.68(m, 4H), 3.56, 3.39(d, 16H), 4.0(m, 2H), 2.69(t, 4H), 2.69(t, 4H), 1.82–1.50(m, 12H); Electrospray LRMS: Calculated for $C_{38}H_{54}N_6O_6$: MH$^+$: 691; Found: MH$^+$: 691;

cis-1,5-cyclooctylene bis{4-[4-(2-aminoethyl)benzoyl]-1-piperazinecarboxylate] (Compound 17); Electrospray LRMS: Calculated for $C_{36}H_{50}N_6O_6$: MH$^+$: 662.8; Found: MH$^+$: 664;

cis-1,5-cyclooctylene bis {4-[4-(1-aminoprop-2-yl) benzoyl]-1-piperazinecarboxylate} (Compound 18); $^1$H-NMR (300 MHz, DMSO-d$_6$): 7.33(s, 8H), 4.6(m, 2H), 3.35–3.06(m, 18H), 2.97(m, 4H), 1.73–1.5(m, 12H), 1.22 (d, 6H), 1.82–1.50(m, 12H); Electrospray LRMS: Calculated for $C_{36}H_{54}N_6O_6$: MH$^+$: 691; Found: MH$^+$: 692;

cis-1,5-cyclooctylene bis{4-[4-(2-aminoethyl)piperid-1-yl]-1-piperazinecarboxylate} (Compound 19); $^1$H-NMR (300 MHz, DMSO-d$_6$): 3.62(d, 8H), 3.42, 3.19(s, 16H), 2.97(t, 4H), 2.82(t, 4H), 1.77–1.55(m, 24H), 1.13(m, 4H); Electrospray LRMS: Calculated for $C_{34}H_{60}N_8O_6$: MH$^+$: 676.9; Found: MH$^+$: 677;

cis-1,5-cyclooctylene bis{4-[trans-4-(2-aminoethyl) cyclohexylacetyl]-1-piperazinecarboxylate} (Compound 20); $^1$H-NMR (300 MHz, DMSO-d$_6$): 3.52(m, 16H), 2.97(t,4H), 2.39(d, 4H), 1.81–1.5(m, 34H), 1.32(m, 6H), 0.99(m, 2H); Electrospray LRMS: Calculated for $C_{38}H_{64}N_6O_6$: MH$^+$: 703; Found: MH$^+$: 703;

trans-1,4-cyclohexylene bis[4-(4-guanidinobenzylcarbamoyl)-1- piperazinecarboxaldehyde] (Compound 21); Electrospray LRMS: Calculated for $C_{32}H_{44}N_{12}O_4$: $MH^+$: 688.8; Found: $MH^+$: 689; and cis-1,5-cyclooctylene bis {4-[4-(2-aminoethyl) cyclohexylcarbonyl]-1-piperazinecarboxylate) (Compound 22); $^1$H-NMR (300 MHz, DMSO-$d_6$): 3.56, 3.49(d, 16H), 2.96(t,4H), 1.77(m, 20H), 1.51(m, 6H), 1.33(m,6H), 1.01(m, 4H); Electrospray LRMS: Calculated for $C_{36}H_{62}N_6O_6$: $MH^+$: 674.9; Found: $MH^+$675.

Proceeding in a fashion analogous to the procedure described in Example 3, Method B, and substituting different starting materials, the following compounds of the invention were prepared:

trans-1,4-cyclohexylenedimethylene bis{4-[4 (aminomethyl)piperid-1-ylcarbonylaminomethyl]-1-piperidinecarboxylate} (Compound 23); $^1$H-NMR (300 MHz, DMSO-$d_6$): 8.0(s, 4H), 6.5(s, 2H), 4.5(m, 8H), 3.9(m, 4H), 3.8(m, 2H), 2.8(s, 2H), 2.6(m, 16H), 1.6(m, 16H), 1.0(m, 10H);

cis-1,5-cyclooctylene bis[4-(4-amidinophenylacetyl)-1-piperazinecarboxylate) (Compound 24); Electrospray LRMS: Calculated for $C_{34}H_{48}N_8O_6$: $MH^+$: 688.8; Found: $MH^+$: 689.6;

cis-1,5-cyclooctylene bis{4-[4-(aminomethyl)piperid-1-ylcarbonylamino]butylaminocarboxylate} (Compound 25); $^1$H-NMR (300 MHz, DMSO-$d_6$): 8.1(s, 6H), 7.0(s, 2H), 4.6(s, 2H), 4.2(m, 12H), 3.9(d, 4H), 2.9(m, 8H), 2.6(m, 8H), 1.6(m, 20H), 1.3(s, 6H), 1.0(m, 4H), Electrospray LRMS: Calculated for $C_{31}H_{64}N_8O_6$: $MH^+$: 652.9; Found: $MH^+$: 653.7;

cis-1,5-cyclooctylene bis{4-[4-(aminomethyl)piperid-1-ylcarbonylaminomethyl)-1-piperidinecarboxylate} (Compound 26); $^1$H-NMR (300 MHz, DMSO-$d_6$): 8.1(s, 6H), 6.5(s, 2H), 4.6(s, 4H), 4.0(m, 24H), 2.9(d, 4H), 2.6(m, 12H), 1.6(m, 20H), 0.9(m, 14H): Electrospray LRMS: Calculated for $C_{34}H_{64}N_8O_6$: $MH^+$: 705; Found: $MH^+$: 706.6;

cis-1,5-cyclooctylene bis[4-(1-amidinopiperid-4-ylmethylcarbamoyl)-1-piperazinecarboxylate] (Compound 27); $^1$H-NMR (300-MHz, DMSO-$d_6$): 7.2(s, 8H), 6.6(m, 2H), 4.6(m, 4H), 3.8(d, 6H), 3.4(m, 31H), 2.9(m, 8H), 1.7(m, 16H), 1.1(m, 4H);

cis-1,5-cyclooctylene bis[4-(4-amidinobenzylcarbamoyl)-1piperazinecarboxylate] (Compound 28); $^1$H-NMR (300 MHz, DMSO-$d_6$): 9.4(s, 4H), 7.8(d, 4H), 7.6(d, 4H), 7.4(m, 2H), 4.8(m, 2H), 4.4(m, 4H), 3.4(m, 40H), 1.8(m, 10H);

trans-2,6-(4,8-dioxabicyclo[3.3.0]octylene) bis[4-(4-guanidinobenzylcarbamoyl)-1-piperazinecarboxylate] (Compound 29); Electrospray LRMS: Calculated for $C_{34}H_{46}N_{12}O_8$: $MH^+$: 751.8; $MH_2^{+2}/2$; 376.4; Found: $MH^+$: 751.2; $MH_2^{+2}/2$; 376.4;

trans-2,3-bicyclo[2.2.2]oct-5-enylenedimethylene bis(4-(4guanidinobenzylcarbamoyl)-1-piperazinecarboxylate] (Compound 30); Electrospray LRMS: Calculated for $C_3H_{52}N_2O_6$: $MH^+$: 773.9; $MH_2^{+2}/2$; 387.5; Found: $MH^+$:773.2; $MH_2^{+2}/2$: 387.2;

cis-1,5-tetracyclo[3.3.1.1$^{3,7}$]decylenedimethylene bis[4-(4-guanidinobenzylcarbamoyl)-1-piperazinecarboxylate] (Compound 31); Electrospray LRMS: Calculated for $C_{40}H_{58}N_{12}O_4$: $MH^+$: 768; $MH_2^{+2}/2$; 384.5; Found: $MH^+$: 769.4; $MH_2^{+2}/2$: 385.4; and cis-1,5-cyclooctylene bis[4-(4-amidinobenzoylaminomethyl)-1-piperidinecarboxylate] (Compound 44); $^1$H-NMR (300 MHz, DMSO-$d_6$): 9.43 (s, 2H), 9.16 (s, 2H), 8.77 (t, 1H), 8.00 (d, 4H), 7.86 (d, 2H), 4.61 (br s, 1H), 3.91(br d, 2H), 3.14 (br s, 2H), 2.69 (br s, 2H), 1.79–1.54 (m, 8H), 1.51–1.42 (m, 1H), 0.99 (q, 2H); Electrospray LRMS: Calculated for $C_{38}H_{54}N_8O_6$: $MH^+$: 716.9; $MH_2^{+2}/2$; 358.5; Found: $MH^+$: 717.5; $MH_2^+$ 2/2: 359.5;

cis-1,5-cyclooctylene bis[4-(4-amidinopiperid-1-ylcarbonylaminomethyl)-1-piperidinecarboxylate] (Compound 45); $^1$H-NMR (300 MHz, DMSO-$d_6$): 8.8 (d, 4H), 6.57 (s, 1H), 4.61 (s, 1H), 4.06 (d, 2H), 3.9 (d, 2H), 2.84 (br s, 2H), 2.73–2.5 (m, 4H), 1.77–1.4 (m, 10H), 0.89 (q, 2H); Electrospray LRMS: Calculated for $C_{36}H_{66}N_{10}O_6$: $MH^+$: 732.9; $MH_2^{+2}/2$; 366.9; Found: $MH^+$: 731.6; $MH_2^{+2}/2$: 366.5; and cis-1,5-tetracyclo[3.3.1.1$^{3,7}$]decylenedimethylene bis(4-(4-guanidinobenzylcarbamoyl)-1-piperazinecarboxaldehyde] (Compound 32); Electrospray LRMS: Calculated for $C_{40}H_{58}N_{12}O_6$: $MH^+$: 801.9; Found: $MH^+$: 802.1; 1,2-cyclohexylene bis[4-(4-guanidinobenzylcarbamoyl)-1-piperazinecarboxadehyde] (Compound 46); Electrospray LRMS; Calculated for $C_{34}H_{48}N_{12}O_4$: $MH^{+2}/2$: 345.7; Found: $MH^{+2}/2$: 345.3;

1,4-bicyclo[2.2.2]octylenedimethylene bis[4(4-guanidinobenzylcarbamoyl)-1-piperazinecarboxylate] (Compound 47); Electrospray LRMS: Calculated for $C_{38}H_{54}N_{12}O_6$: $MH^{+2}/2$: 388.3; Found: $MH^{+2}$: 388.3;

cis-1,5-cyclooctylene bis[4-(4-guanidinophenylcarbonylaminomethyl)-1-piperidinecarboxylate] (Compound 48); Electrospray LRMS: Calculated for $C_{38}H_{54}N_{10}O_6$: $MH^{+2}$: 374.5; Found: $MH^{+2}/2$: 374.6; and cis-1,4-cyclohexylenedimethylene bis[4(4-guanidinobenzylcarbamoyl)-1-piperazinecarboxylate) (Compound 49); Electrospray LRMS Calculated for $C_{36}H_{52}N_{12}O_6$; $MH^{+2}/2$; 375.4; Found: $MH^{+2}/2$; 375.1.

Example 4 cis-1,5-Cyclooctylene bis[4-((trans-4-aminomethylcyclohexylens methylene)carbamoyl)-1-piperazinecarboxylate] (Compound 4)

The following example describes the preparation of a compound if this invention in which Z is amino, $X^1$ is —$X^6$—$X^7$—$X^8$— (wherein n6 is 1, $X^7$ is trans-1,4-cyclohexylene), $X^2$ is —NHC(O)—, $X^3$ is 1,4-piperazinylene, $X^4$ is —C(O)O— and Y is cis-1,5-cyclooctylene.

trans-4-(Aminomethyl)cyclohexanemethanol hydrochloride

A 1.0 M solution of borane in tetrahydrofuran (250 mL, 260 mmol.) was added slowly dropwise to a suspension of trans-4-(aminomethyl)cyclohexanecarboxylic acid (10.0 g, 64.0 mmol.) in tetrahydrofuran (250 mL). Gas evolution was observed. The reaction mixture was heated at reflux for 14 hours. The resulting solution was cooled to 0° C. and carefully treated dropwise with 1 N methanolic hydrochloric acid (250 mL). Gas evolution was observed. The white suspension obtained was stirred for 1 hour at 23° C. and subsequently concentrated. Methanol was added to the residue and the suspension was concentrated. This procedure was repeated twice to give trans-4-(Aminomethyl) cyclohexanemethanol hydrochloride (10.6 g, 93% yield) as a white solid.

$^1$H NMR (CD$_3$OD): 3.38 (d, 2H), 2.71 (d, 2H), 1.88 (d, 4H), 1.48 (m, 2H), 1.01 (m, 2H)

N-tert-Butoxycarbonyl-trans-4-(aminomethyl) cyclohexanemethanol

Sodium carbonate (1.33 g, 12.4 mmol.) was added to a solution of trans-4-(aminomethyl)cyclohexanemethanol hydrochloride (1.5 g, 8.3 mmol.) in 1:1 dioxane:water (40 mL). Di-tert-butyl dicarbonate (2.0 g, 9.13 mmol.) was added to the reaction mixture at 0° C. The reaction mixture was stirred at room temperature for 5 hours then partitioned between 10% methanol in dichloromethane and water. The organic layer was dried over anhydrous sodium sulfate and concentrated. N-tert-Butoxycarbonyl-trans-4-(aminomethyl)cyclohexanemethanol (1.97 g, 98% yield) was obtained as a white solid.

$^1$H NMR (CDCl$_3$): 4.58 (br, 1H), 3.44 (d, 2H), 2.95 (tr, 2H), 1.81 (m, 4H), 1.54 (m, 2H), 1.44 (s, 9H), 0.92 (tr, 4H)

N-tert-Butoxycarbonyl-trans-4-(aminomethyl) cyclohexanemethyl tosylate p-Toluenesulfonyl chloride (3.3 g, 17.0 mmol) was added to a solution of N-tert-butoxycarbonyl-trans-4-(aminomethyl)cyclohexanemethanol (3.5 g, 14.0 mmol) in pyridine (20 mL) containing 4 Å sieves and the reaction mixture was stirred at 23° C. for 23.5 hours. The resulting white suspension was concentrated and the residue obtained partitioned between dichloromethane and 0.05 N hydrochloric acid. The organic layer was dried over sodium sulfate and concentrated. Crude N-tert-butoxycarbonyl-trans-4-(aminomethyl)cyclohexanemethyl tosylate (5.73 g) was obtained as a yellow solid.

$^1$H NMR (CDCl$_3$): 7.78 (d, 2H), 7.34 (d, 2H), 4.56 (br, 1H), 3.82 (d, 2H), 2.94 (tr, 2H), 2.48 (s, 3H), 1.74 (d, 4H), 1.64 (m, 2H), 1.48 (s, 9H), 0.91 (tr, 4H)

N-tert-Butoxycarbonyl-trans-4-(aminomethyl) cyclohexanemethyl azide

Sodium azide (4.7 g, 70.0 mmol.) was added to a solution of N-tert-butoxycarbonyl-trans-4-(aminomethyl)cyclohexanemethyl tosylate (5.73 g, 14.0 mmol.) in DMF (50 mL) containing 4 Å sieves and the resulting suspension stirred at 23° C. for 190 hours followed by concentration. The residue obtained was partitioned between dichloromethane and water. The organic layer was dried over anhydrous sodium sulfate and concentrated. N-tert-Butoxycarbonyl-trans-4-(aminomethyl)cyclohexanemethyl azide (3.22 g, 86% yield) was obtained as a yellow oil.

$^1$H NMR (CDCl$_3$): 3.14 (d, 2H), 2.99 (tr, 2H), 1.82 (tr, 4H), 1.51 (m, 2H), 1.48 (s, 9H), 0.99 (m, 4H)

N-tert-Butoxycarbonyl-trans-1,4-cyclohexane bis (methylamine) hydrochloride

Ethanol (40 mL) was added to N-tert-butoxycarbonyl-trans-4-(aminomethyl)cyclohexanemethyl azide (1.79 g, 6.67 mmol.) and 5% palladium on carbon (270 mg, 0.15 wt. %) under nitrogen. The reaction mixture was stirred under hydrogen at atmospheric pressure for 6 hours at 23° C. The black suspension was filtered and the filtrate concentrated to give N-tert-butoxycarbonyl-trans-1,4-cyclohexane bis (methylamine) as a yellow oil. The crude amine was taken up into methanol (2.0 mL) followed by addition of hydrogen chloride in dioxane (4.0 M, 2.0 mL, 8.0 mmol.) and ethyl ether (25 mL). The resulting precipitate was collected by filtration to give N-tert-butoxycarbonyl-trans-1,4-cyclohexanebis(methylamine) hydrochloride (1.42 g, 76% yield) as a colorless solid.

$^1$H NMR (D$_2$O): 3.00–2.80 (m, 4H), 1.90–1.70 (m, 4H), 1.70–1.50 (m, 2H), 1.40 (s, 9H), 1.10–0.90 (m, 4H).

Electrospray LRMS: Calculated for C$_{13}$H$_{27}$N$_2$O$_2$ (MH$^+$): 243 Found: 243

N-tert-Butoxycarbonyl-trans-4-(aminomethyl) cyclohexanemethyl isocyanate

N-tert-Butoxycarbonyl-trans-1,4-cyclohexane bis (methylamine) hydrochloride (1.45 g, 5.2 mmol.) was taken up into dichloromethane (25 mL) followed by addition of pyridine (1.75 mL, 21 mmol) and the mixture was cooled to 0° C. Triphosgene (617 mg, 2.1 mmol.) was subsequently added to the above solution and the mixture was allowed to slowly warm to room temperature over 2 hours. The organic solution was washed with 0.1N aqueous hydrochloric acid (2×25 mL) followed by drying over anhydrous magnesium sulfate and filtration. Concentration gave N-tert-butoxycarbonyl-trans-4-(aminomethyl)cyclohexanemethyl isocyanate (1.38g, 99% yield) as a yellow crystalline solid.

$^1$H NMR (CDCl$_3$): 4.60 (br s, 1H), 3.15 (d, 2H), 2.95 (tr, 2H), 1.85–1.75 (m, 4H), 1.50–1.40 (m, 2H), 1.45 (s, 9H), 1.05–0.90 (m, 4H)

cis-1,5-Cyclooctylene bis[4-((trans-4-tert-butoxycarbonylaminomethylcyclohexylenemethylene) carbamoyl)-1-piperazinecarboxylate]

cis-1,5-Cyclooctylene bis(1-piperazinecarboxylate) bis-hydrochloride (229.7 mg, 0.53 mmol.) and diisopropylethylamine (200 μL, 2.3 mmol.) were dissolved in DMF (4.0 mL) and the mixture cooled to 0° C. N-tert-Butoxycarbonyl-trans-4-(aminomethyl)-cyclohexanemethyl isocyanate (285 mg, 1.06 mmol.) was subsequently added and the mixture was allowed to warm to room temperature over twelve hours. Concentration and addition of dichloromethane (25 mL) to the residue followed by washing the organic solution with 0.1N aqueous hydrochloric acid (2×25 mL) and drying over anhydrous magnesium sulfate gave the crude product. Filtration and concentration afforded cis-1,5-cyclooctylene bis[4-((trans-4-tert-butoxycarbonylaminomethylcyclohexylene methylene) carbamoyl)-1-piperazinecarboxylate] (534 mg, 56% yield) as a colorless solid.

$^1$H NMR (CDCl$_3$): 4.80 (m, 2H), 4.70 (tr, 2H), 4.65 (tr, 2H), 3.45 (m, 8H), 3.35 (m, 8H), 3.10 (tr, 4H), 2.95 (tr, 4H), 1.95–1.50 (m, 24H), 1.45 (s, 18H), 1.00–0.90 (m, 8H).

cis-1,5-Cyclooctylene bis[4-((trans-4-aminomethylcyclohexylenemethylene)carbamoyl)-1-piperazinecarboxylate] (Compound 4)

cis-1,5-Cyclooctylene bis[4-((trans-4-tertbutoxycarbonylaminomethylcyclohexylenemethylene) carbamoyl)-1piperazinecarboxylate] (534 mg, 0.59 mmol.) was treated with trifluoroacetic acid (5 mL) and the mixture was concentrated in vacuo to a red oil after 15 minutes. The crude material was taken into water (10 mL) and the aqueous suspension filtered through Millipore filter paper type GV (0.22 μm) to give a yellow solution. Purification by preparative reverse phase HPLC and lyophilization gave cis-1,5-cyclooctylene bis[4((trans-4-aminomethylcyclohexylenemethylene)carbamoyl)-1-piperazinecarboxylate (Compound 4) bis-hydrochloride as a nearly colorless solid.

$^1$H-NMR (300 MHz, DMSO-d$_6$): 8.00 (br s, 6H), 6.60 (m, 2H), 4.65 (m, 2H), 3.40 (s, 8H), 3.30 (s, 8H), 2.85 (m, 4H), 2.60 (tr, 4H), 1.80–1.30 (m, 24H), 0.90–0.70 (m, 8H).

Electrospray LRMS: Calculated for C$_{36}$H$_{64}$N$_8$O$_6$: MH$^+$706.0; MH$_2$$^{+2}$/2: 353.5Found: MH$^+$: 705.7; MH$_2$$^{+2}$/2: 353.3

Proceeding in a fashion analogous to the procedure described in Example 4 and substituting different starting materials, the following compounds of the invention were prepared:

cis-1,5-cyclooctylene bis{4-[2-(4-amidinophenyl)ethyl carbamoyl]-1-piperazinecarboxylate} (Compound 33)
$^1$H-NMR (300 MHz, DMSO-d$_6$): 9.3(s, 4H), 9.0(s, 4H), 7.7(d, 4H), 7.4(d, 4H), 6.7(t, 2H), 4.6(m, 2H), 3.8(m, 52H), 2.8(t, 4H), 1.7(m, 10H);

cis-1,5-cyclooctylene bis[4-(5-aminopentylcarbamoyl)-1-piperazinecarboxylate] (Compound 34); Electrospray LRMS: Calculated for C$_{30}$H$_{56}$N$_8$O$_6$: MH$^+$: 625.8; Found: MH$^+$: 625.7;

cis-1,5-cyclooctylene bis(4-(6-aminohexylcarbamoyl)-1-piperazinecarboxylate] (Compound 35); Electrospray LRMS: Calculated for C$_{32}$H$_{60}$N$_8$O$_6$: MH$^+$: 653.9; Found: MH$^+$: 654.2;

cis-1,5-cyclooctylene bis[4-(5-amino-2-pentenylcarbamoyl)-1-piperazinecarboxylate] (Compound 36); Electrospray LRMS: Calculated for $C_{30}H_{52}N_8O_6$: MH$^+$: 621.8; Found: MH$^+$: 621.5;

cis-1,5-cyclooctylene bis(4-(4-aminobutylcarbamoyl)-1-piperazinecarboxylate] (Compound 37); Electrospray LRMS: Calculated for $C_{28}H_{52}N_8O_6$: MH$^+$: 597.8; Found: MH$^+$: 596.9;

cis-1,5-cyclooctylene bis{4-[2-(2-aminoethoxy)ethylcarbamoyl]1-piperazinecarboxylate} (Compound 38); Electrospray LRMS: Calculated for $C_{28}H_{52}N_8O_8$: MH$^+$: 628.8; Found: MH$^+$: 628.5;

cis-1,5-cyclooctylene bis(4-[trans-4-aminomethylcyclohexylaminoformyloxy)-1-piperidinecarboxylate] (Compound 39); Electrospray LRMS: Calculated for $C_{36}H_{62}N_6O_8$: MH$^+$: 706.9; Found: MH$^+$: 707.7;

cis-1,5-cyclooctylene bis[N-2-(trans-4-aminomethylcyclohexylaminoformyloxy)ethyl-N methylaminocarboxylate] (Compound 40); Electrospray LRMS: Calculated for $C_{32}H_{58}N_6O_8$: MH$^+$: 654.9; Found: MH$^+$; 655;

cis-1,5-cyclooctylene bis[N-2- (trans-4-aminomethylcyclohexylmethylaminoformyloxy)ethyl-N methylaminocarboxylate} (Compound 41); Electrospray LRMS: Calculated for $C_{34}H_{62}N_6O_8$: MH$^+$: 683.9; Found: MH$^+$: 683.5;

trans-1,4-cyclohexylenedimethylene bis[4-(trans-4-aminomethylcyclohexylmethylcarbamoyl)-1-piperazinecarboxylate] (Compound 42); Electrospray LRMS: Calculated for $C_{36}H_{64}N_8O_6$: MH$^+$: 706; Found: MH$^+$: 704.6; and cis-1,5-cyclooctylene bis[4-(trans-4-aminomethylcyclohexylmethylaminoformyloxy)-1-piperidinecarboxylate] (Compound 43); Electrospray LRMS: Calculated for $C_{38}H_{64}N_6O_8$: MH$^+$: 736; Found: MH$^+$: 735.6.

Example 5 cis-5-[4-(5-aminopentylcarbamoyl)piperazin-1-ylformyloxy]cyclooctyl 4-(4-guanidinobenzylcarbamoyl)-1-piperazinecarboxylate (Compound 50)

The following example describes the preparation of an unsymmetrical compound of this invention in which R$^2$ is 4-(4-aminobutylcarbamoyl)piperazin-1-ylformyloxy, R$^3$ is 4-(4-aminobutylcarbamoyl)piperazin-1-ylformyloxy and Y is cis1,5-cyclooctylene.

cis-1,5-Cyclooctylenediol bischloroformate (1.91 g, 7.1 mmol) was taken into dichloromethane (20 mL) and a solution of tert-butyl 1-piperazinecarboxylate (1.3 g, 7.1 mmol) and diisopropylethylamine (1.3 mL, 7.1 mmol) in dichloroethane (10 mL) was added dropwise. The mixture was stirred 10 minutes at room temperature and then aqueous hydrochloric acid (0.1M, 30 mL) was added. The organic layer was separated, dried (anhydrous ammonium sulfate), filtered and concentrated. Purification of the residue by silica gel flash chromatography eluting with ethyl ether/hexane (1:1) gave cis-5-chloroformyloxycyclooctyl 4-tert-buxtoxycarbonyl-1-piperazinecarboxylate (663.1 mg, 1.6 mmol) as a colorless oil.

tert-Butyl-4-(4-guanidinobenzylcarbamoyl)-1-piperazinecarboxylate (383.7 mg, 1.1 mmol) was treated with neat trifluoroacetic acid (2 mL) at room temperature until a homogenous solution was obtained. The solution was concentrated in vacuo to a thick oil. The oil was taken into water (10 mL) and 5M aqueous sodium hydroxide was added dropwise until the solution was pH 7.5–8.0. cis-5-Chloroformyloxycyclooctyl 4-tert-buxtoxycarbonyl-1-piperazinecarboxylate (447.7 mg, 1.1 mmol) in THF (3 mL) was added to the solution with rapid stirring and while continuing to add 5M sodium hydroxide to maintain pH 7.5–8.0. 5M Sodium hydroxide (10 mL) was added to adjust the solution to pH 14 and then ethyl ether (1 mL) was added. The mixture was allowed to stand for 15 minutes at room temperature giving a white solid. The solid was collected by filtration and washed with ice water (1×), acetonitrile (1×) and ethyl ether (1×) and dried to give cis-5-(4-tert-butoxycarbonylpiperazin-1-ylformyloxy)cyclooctyl 4-guanidinobenzylcarbamoyl-1-piperazinecarboxylate (527.2 mg, 0.85 mmol) as a white solid.

cis-5-(4-tert-Butoxycarbonylpiperazin-1-ylformyloxy) cyclooctyl 4-guanidinobenzylcarbamoyl-1-piperazinecarboxylate (129 mg, 0.196 mmol) was treated with neat trifluoroacetic acid (1 mL) until a homogenous solution was obtained. The solution was concentrated in vacuo to a colorless oil. The oil was taken into N,N-dimethylformamide (2 mL) and then diisopropylethylamine (340 μL, 2 mmol) was added. 5-(tert-butoxycarbonyl) aminopentyl isocyanate (44 mg, 0.2 mmol) in N,N-dimethylformamide (500 μL) was added to the solution and the mixture was stirred 12 hours at room temperature. The mixture was concentrated in vacuo and the residue was combined with water (5 mL) and treated with trifluoroacetic acid (2 mL) until a homogenous solution was obtained. The solution was concentrated in vacuo and the residue was taken into water (5 mL). Purification by preparative HPLC and subsequent lyophilization gave cis-5-[4(5-aminopentylcarbamoyl)piperazin-1-ylformyloxy]cyclooctyl 4-(4-guanidinobenzylcarbamoyl)-1-piperazinecarboxylate as a colorless oil.

Electrospray LRMS: Calculated for $C_{33}H_{54}N_{10}O_6$: MH$^+$: 687.9; Found: MH$^{+2}$: 687.6.

Proceeding in a fashion analogous to the procedure described in Example 5 or by other methods described herein and substituting different starting materials the following compounds of the invention were prepared:

cis-5-[4-(4-aminobutylcarbamoyl)piperazin-1-ylformyloxy] cyclooctyl 4-(4-guanidinobenzylcarbamoyl)-1-piperazinecarboxylate (Compound 51); Electrospray LRMS:Calculated for $C_{32}H_{52}N_{10}O_6$: MH$^{+: 673.8}$; Found: MH$^+$: 673.8;

cis-5-[4-(4-trans-aminomethylcyclohexylmethylcarbamoyl) piperazin-1-ylformyloxy)]cyclooctyl 4-(4-guanidinobenzylcarbamoyl)-1-1piperazinecarboxylate (Compound 52); Electrospray LRMS: Calculated for $C_{36}H_{57}N_{10}O_6$: MH$^{+: 726.9}$; Found: MH$^+$: 727.3;

cis-5-[4-(3-aminopropylcarbamoyl)piperazin-1-ylformyloxy]cyclooctyl 4-(4-guanidinobenzylcarbamoyl)-1-piperazinecarboxylate (Compound 53); Electrospray LRMS: Calculated for $C_{31}H_{50}N_{10}O_6$: MH$^+$: 659.8; Found: MH$^+$: 659.2; and cis-5-[4-(6-aminohexylcarbamoyl)piperazin-1-ylformyloxy)cyclooctyl 4-(4-guanidinobenzylcarbamoyl)-1-piperazinecarboxylate (Compound 54); Electrospray LRMS: Calculated for $C_{34}H_{54}N_9O_6$: MH$^+$: 686.9; Found: MH$^+$: 686.4.

Example 6 cis-1,5-Cyclooctylene bis(4-{4-[1,2,3-tri(1-acetoxyethoxycarbonly)guanidino]benzylcarbamoyl}-1-piperazinecarboxylate)

The following example describes the preparation of a prodrug derivative of a compound of the invention in which Z is guanidino, X$^1$ is —X$^6$—X$^7$—X$^8$—, wherein n6 is 0, n8 is 1 and X$^7$ is 1,4-phenylene, X$^2$ is —NHC(O)—, X$^3$ is 1,4-piperazinylene, $X^4$ is —C(O)O—, Y is cis-1,5-cyclooctylene and $R^4$ is 1-acetoxyethoxycarbonyl.

cis-1,5-Cyclooctylene bis[4-(4-guanidinobenzylcarbamoyl)-1-piperazinecarboxylate] (49 mg, 0.065 mmol) was suspended in N,N-dimethylformamide (2 mL) and diisopropylethylamine (50 mL, 0.26 mmol) and acetoxyethyl paranitrophenylcarbonate (70.4 mg, 0.26 mmol) was added sequentially. The mixture was stirred 1 hour at room temperature and then concentrated in vacuo. The residue was taken up into dichloromethane (25 mL) and the solution was washed with saturated aqueous sodium dicarbonate (2x) and 0.1M aqueous hydrochloric acid (1x), dried (anhydrous magnesium sulfate), filtered and concentrated. The residue was purified by silica gel flash chromatography eluting with ethyl ether following with ethyl acetate/ethanol (20:1). Concentrating gave cis-1,5-cyclooctylene bis(4-{4-[1,2,3-tri(1-acetoxyethoxycarbonyl)guanidino)benzylcarbamoyl}-1-piperazinecarboxylate] (40 mg, 0.031 mmol) as a colorless solid.

Electrospray LRMS: Calculated for $C_{56}H_{76}N_{12}O_{22}$: $MH^+$: 1269:3; Found: $MH^+$: 1269.4.

Proceeding in a fashion analogous to the procedure described in Example 6 or by other methods described herein and substituting different starting materials the following prodrug derivatives of compounds of the invention were prepared:

cis-5-[4-(5-N-acetylglycylaminopentylcarbamoyl) piperazin-1-ylformyloxy]cycloocty] 4-guanidinobenzylcarbamoyl-1-piperazinecarboxylate); Electrospray LRMS: Calculated for $C_{37}H_{59}N_{11}O_8$: $MH^+$: 786.9; Found: $MH^+$: 786.5; and cis-1,5-cyclooctylene bis(4-{4-[1,2-di(1-acetoxyethoxycarbonyl)amidino]benzylcarbamoyl}-1-piperazinecarboxylate]); Electrospray LRMS: Calculated for $C_{64}H_{92}N_{12}O_{22}$: $MH^+$: 1381.7; Found: $MH^+$: 1403.

VI. In Vitro Tryptase Inhibition Assay

The compounds to be assayed (approximately 1 mg) were dissolved in 200 µL dimethylsulfoxide (DMSO) and diluted 1:10 into buffer containing 50 millimolar (mM) Tris-HCl (pH 8.2), 100 mM sodium chloride, and 0.05% polyoxyethylenesorbitan monolaurate (Tween-20°, available from Sigma, St. Louis, Mo.). Seven additional threefold dilutions were made from the initial dilution into the same buffer supplemented with 10% DMSO. Aliquots (50 microliters, µL) from each of the eight dilutions in the series were transferred to individual wells in a 96-well U-bottom microtiter plate. 25 µL of a stock solution of tryptase was added to each well and the samples were mixed and incubated for one hour at room temperature (tryptase was purified from human lung and skin tissue preparations, HMC-1 (human mast cell line) and also obtained from commercial sources (ICN Biomedicals, Irvine, Calif.; Athens Research & Technology, Athens, Ga.)). Each inhibitor had similar affinity to tryptase from all of these sources. The tryptase solution was prepared by placing 60 µg/mL of tryptase into solution with 10 mM MES (2-[N-Morpholino]ethane sulfonic acid) containing 2 mM $CaCl_2$, 20% glycerol and 50 µg/mL heparin. The enzyme reaction was initiated with the addition of the synthetic tripeptide substrate, tosyl-Gly-Pro-Lys-p-nitroanilide (available from Sigma, 25 µL; 0.5 mM final concentration). The microtiter plates were immediately transferred to a UV/MAX Kinetic Microplate Reader (Molecular Devices) and hydrolysis of the chromogenic substrate was followed spectrophotometrically at 405 nanometers (nM) for five minutes. The enzyme assays routinely yielded linear progress curves under these conditions. Initial velocity measurements calculated from the progress curves by a kinetic analysis program (BatchKi; Petr Kuzmic, University of Wisconsin, Madison, Wis.) were used to determine apparent inhibition constants for compounds 1, 2 and 4.

A potent tryptase inhibitor of the present invention, Compound 3, is classified as a tight binding inhibitor because its apparent affinity for tryptase ($K_i'$ is calculated to be 200 pM using the program BatchKi) is comparable to the enzyme concentration used in the assay. However, $K_i'$ varies with the enzyme concentration used in the enzyme assay. A graphical method (Henderson, P. J. F., Biochem. J. 127, 321 (1972)) was used to determine the $K_i'$ of Compound 3 that is independent of the tryptase concentration. In this experiment, the concentrations of tryptase (0.25, 0.50, 1.0 and 2.0 nM) and Compound 3 (40, 110, 340 and 680 pM) were varied in pre-incubation mixtures for 1 hour before adding substrate (500 µM tosyl-gly-pro-lys-para-nitroanilide). The $IC_{50}$ of Compound 3 was determined at each concentration of tryptase. The y-intercept of a replot of $IC_{50}$ (ordinate) versus tryptase concentration (abscissa) produces a value for $K_i'$. The true dissociation constant of a competitive inhibitor, $K_i$, is calculated from the relationship (See, Morrison, J. F., Methods in Enzymology 63, 437–467 (1969)):

$$K_i=K_i'/(1+S/K_m), \text{ where } S=500 \text{ µM and } K_m=300 \text{ µM}$$

The dissociation constant of Compound 3 from tryptase is calculated to be 60 pM by this method.

The inhibition constants ($K_i'$, micromolar (µM)) were determined for the compounds of the present invention. According to the present invention, a compound was termed "active" or "effective" as a tryptase inhibitor when its $K_i'$ was less than 5 µM.

Proceeding as in the above in vitro assay compounds of the invention were tested and the following $K_i$ (µM) values were obtained: Compound 1 (0.004), Compound 2 (0.002), Compound 3 (0.0002), Compound 4 (0.0158), Compound 5 (0.002), Compound 6 (0.00037), Compound 7 (0.005), Compound 8 (0.03), Compound 9 (0.493), Compound 10 (0.00047), Compound 11 (0.207), Compound 12 (0.26), Compound 13 (0.00013), Compound 14 (1.3), Compound 15 (0.302), Compound 16 (0.0015), Compound 17 (0.0049), Compound 18 (0.713), Compound 19 (1.51), Compound 20 (0.00081), Compound 21 (0.0609), Compound 22 (0.009), Compound 23 (0.119), Compound 24 (0.00016), Compound 25 (0.734), Compound 26 (0.332), Compound 27 (0.614), Compound 28 (0.0087), Compound 29 (0.0038), Compound 30 (0.008), Compound 31 (0.0266), Compound 32 (0.0122), Compound 33 (0.44), Compound 34 (0.011), Compound 35 (1.44), Compound 36 (0.125), Compound 37 (0.508), Compound 38 (0.75), Compound 39 (0.858), Compound 40 (1.39), Compound 41 (1.1), Compound 42 (0.064), Compound 43 (1.45), Compound 44 (0.008), Compound 45 (0.114), Compound 46 (0.772), Compound 47 (0.00042), Compound 48 (2.3), Compound 49 (0.0034), Compound 50 (0.00045), Compound 51 (0.0038), Compound 52 (0.00048), Compound 53 (0.044) and Compound 54 (0.02).

VII. In Vivo Testing

The allergic sheep model of asthma was employed for the in vivo evaluation of the compounds of the invention as antiasthmatics. These methods have been published previously (see Abraham et al. (1983) *Am. Rev. Respir. Dis.* 128:839–844; Allegra et al. (1983) *J. Appl. Physiol.* 55:726–730; Russi et al. (1985) *J. Appl. Physiol.* 59:1416–1422; Soler et al. (1989) *J. Appl. Physiol.* 67:406–413. Each sheep serves as its own control. Body weights for these animals ranged from 20–50 kilograms.

Figure 5:
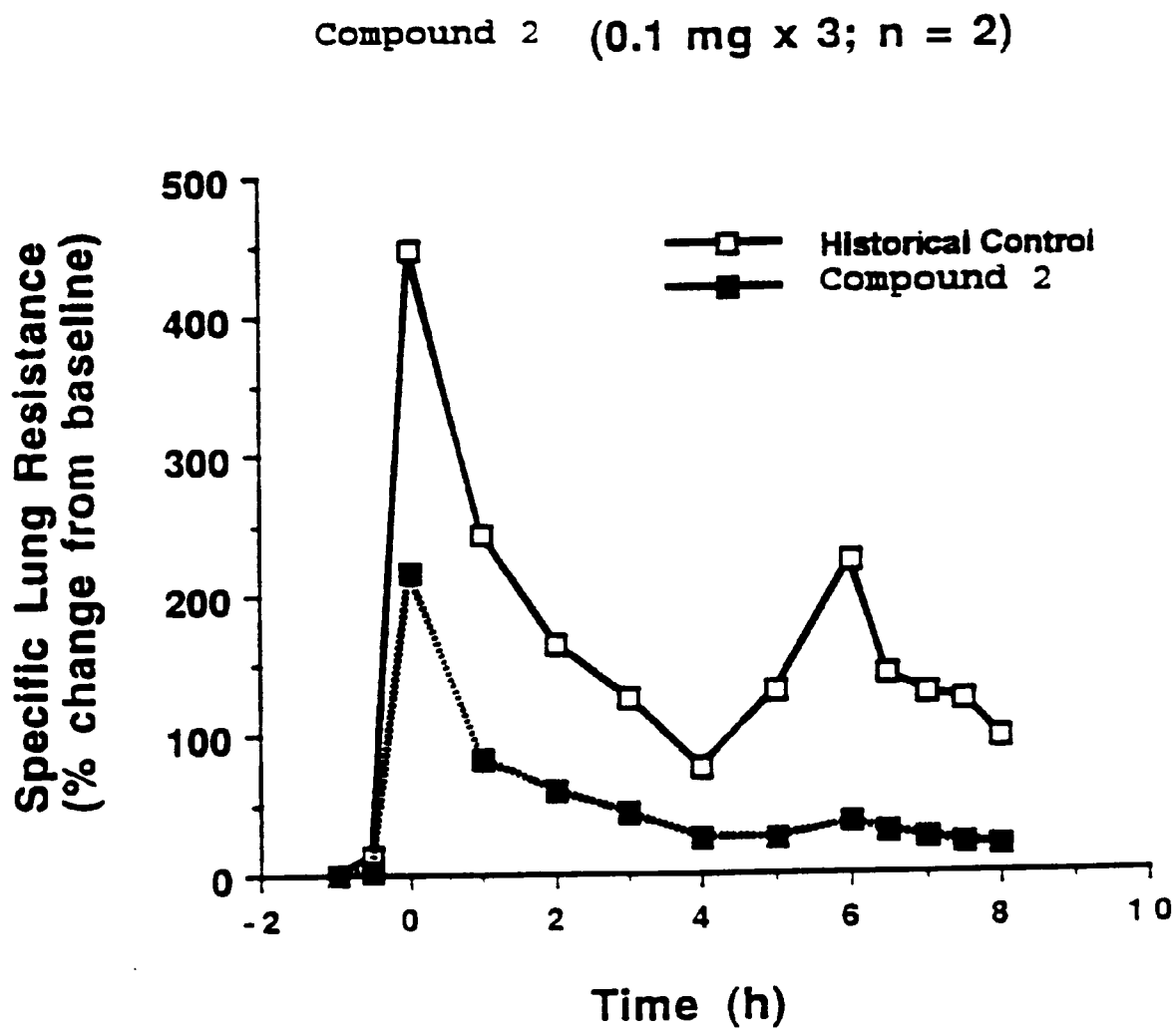
FIG. 5 is a graphical representation of the Specific Lung Resistance (SRL) as a function of time (in hours) of antigen-challenged sheep treated with cis-1,5-cyclooctylene bis(4-guanidinobenzylcarbamoylmethylaminocarboxylate) (Compound 2) by aerosol administration of 3, 0.1 mg doses, versus sheep treated with a control.

In these studies, 50 μg of Compound 3 of the invention was dissolved in buffered saline and the total solution delivered as an aerosol 0.5 hours before, 4 hours after, and 24 hours after antigen challenge (total dose=150 μg; n=3). This compound produced a significant attenuation of the early and late responses to the antigen challenge as measured by Specific Lung Resistance (SRL). This is shown in FIG. 1. Similar results were achieved for Compound 2 as shown in FIG. 5. The peak early response was taken as the average of the maximum values occurring immediately post-challenge. Peak late responses were calculated by averaging the maximum response values obtained for each animal within the 6–8 hour time period. This approach is conservative and eliminates the possible reduction in the late response due simply to averaging.

Figure 2:
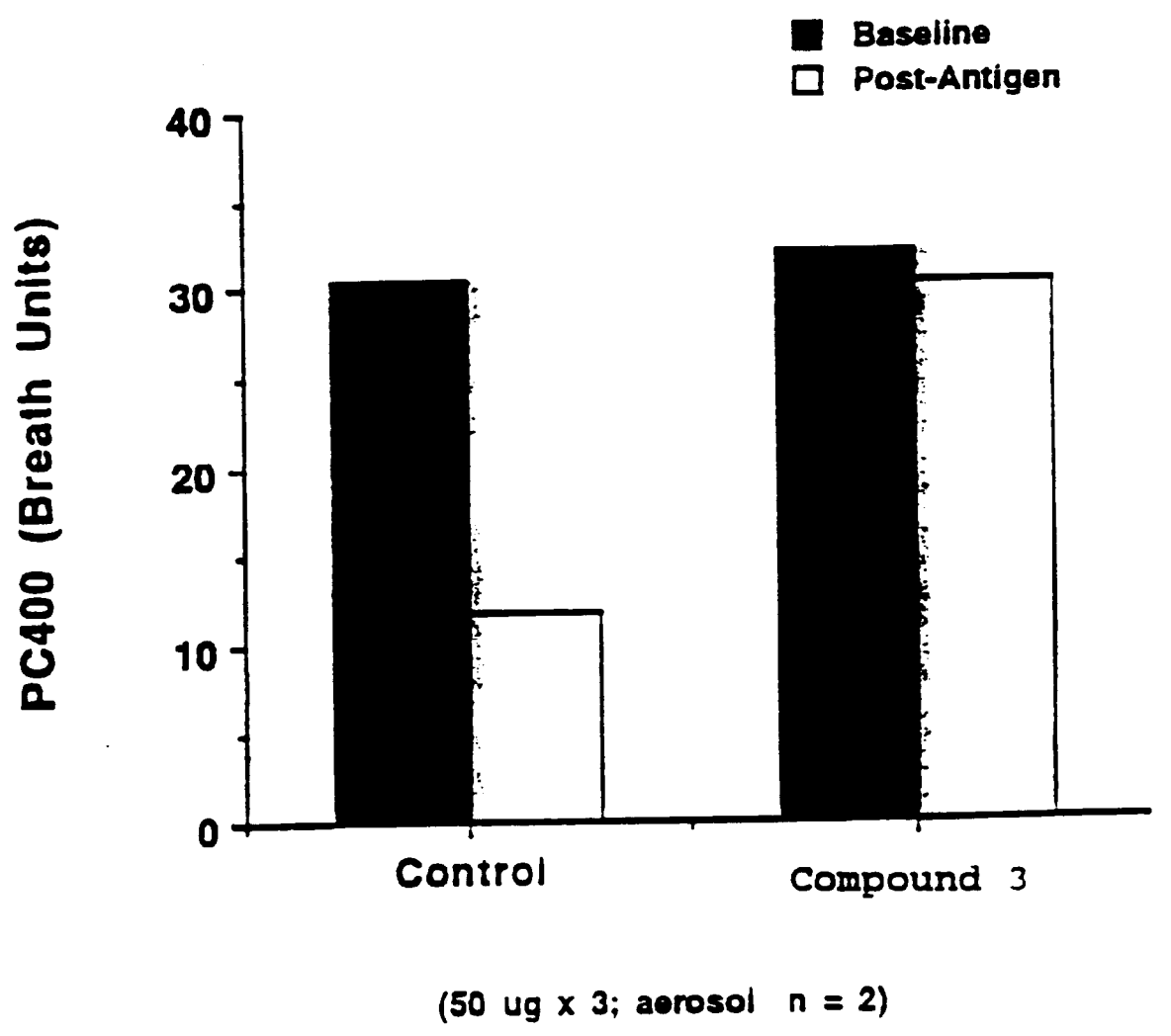
Figure 6:
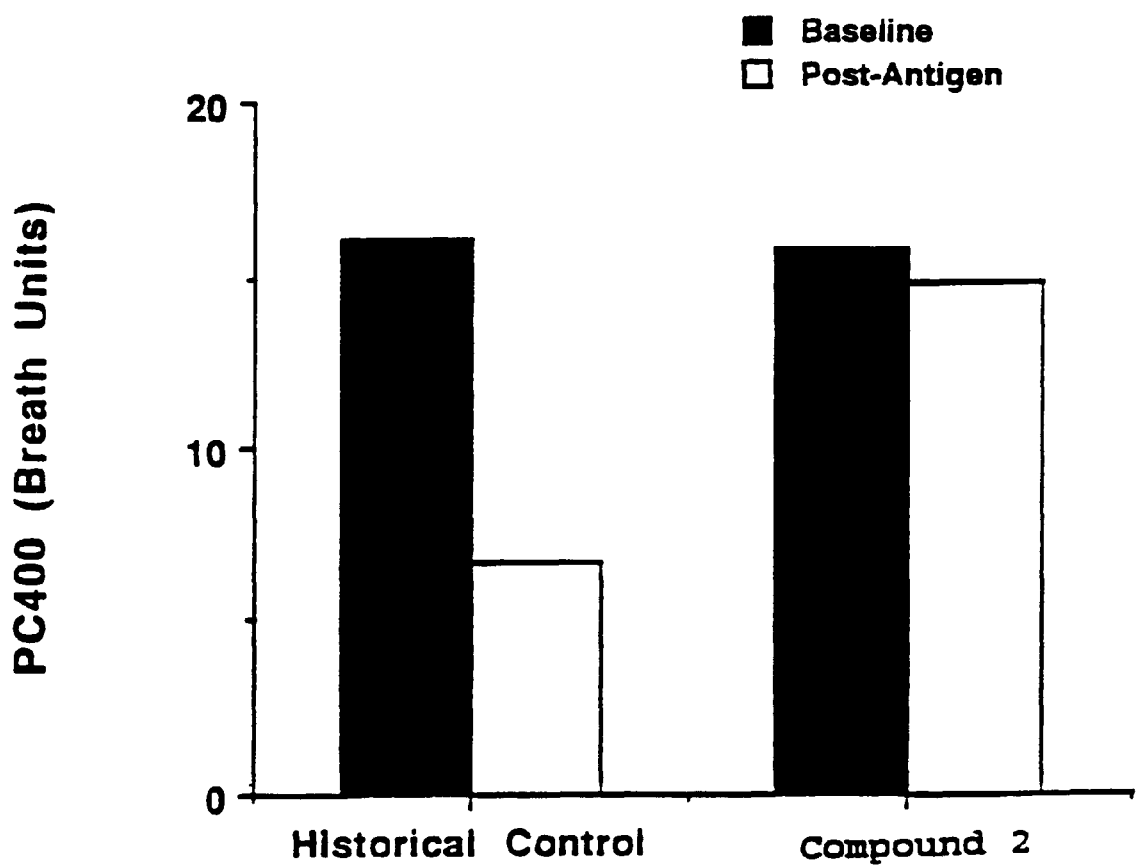
FIG. 6 is a bar chart showing the airway hyperresponsiveness (measured as PC400) antigen-challenged sheep treated with cis-1,5-cyclooctylene bis(4-guanidinobenzylcarbamoylmethylaminocarboxylate) (Compound 2) by aerosol administration of 3, 0.1 mg doses, versus sheep treated with a control.

Twenty-four hours after antigen challenge in both the control and drug trial, the sheep developed airway hyperresponsiveness. Airway hyperresponsiveness is expressed as PC400, the concentration of carbachol that causes a 400% increase in SRL; therefore, a decrease in PC400 indicates hyperresponsiveness. Compound 3 was found to block the onset of hyperresponsiveness. As shown in FIG. 2, this compound maintained the PC400 at substantially the baseline value of 32 breath units. The number of breath units fell to 12 for those animals in the control group. Thus, treatment with Compound 3 of the invention resulted in a significant improvement in airway function in antigen challenged sheep. Likewise, Compound 2 also shows similar results, as shown in FIG. 6.

Compound 3 was also found to possess oral activity. Three doses of the compound (2 mg in 10 mL water) were administered to sheep through an intergastric tube 1 hr before challenge, 4 hours post-challenge, and 24 hours post-challenge. As illustrated in FIG. 5, animals treated with this compound had an early phase SRL of about 175. Untreated animals showed an SRL of about 250. With respect to late phase reaction, animals treated with this compound showed an SRL of about 50 as compared to an SRL of over 200 for untreated animals. Thus, this compound showed significant anti-asthmatic properties when delivered orally.

Figure 7:
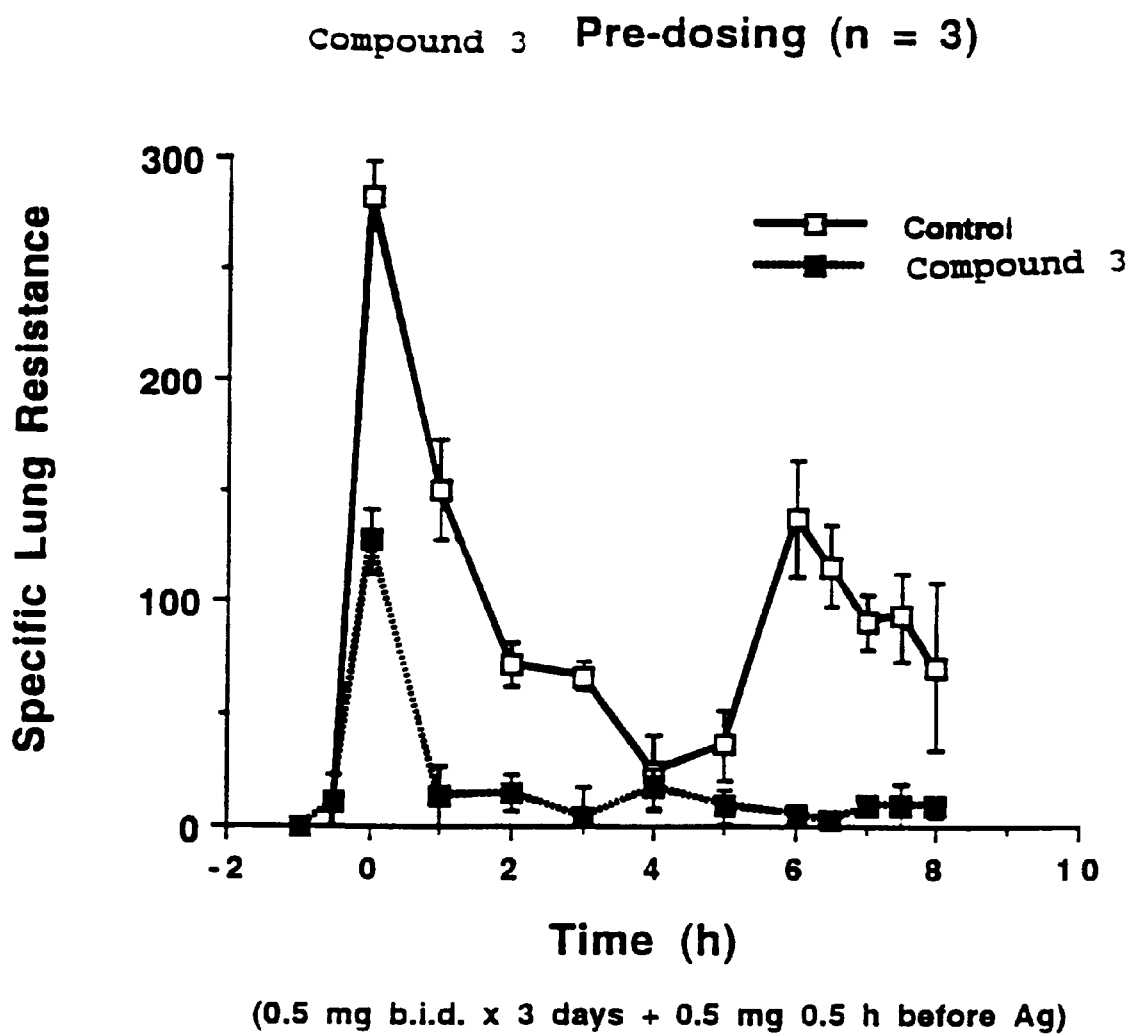
FIG. 7 is a graphical representation of the Specific Lung Resistance (SRL) as a function of time (in hours) of antigen-challenged sheep pretreated with cis-1,5-cyclooctylene bis [4-(4-guanidinobenzylcarbamoyl)-1-piperazinecarboxylate] (Compound 3) by aerosol administration of 0.5 mg per day for three days, with an additional 0.5 mg dose one half hour before antigen challenge, versus sheep treated with a control.
Figure 8:
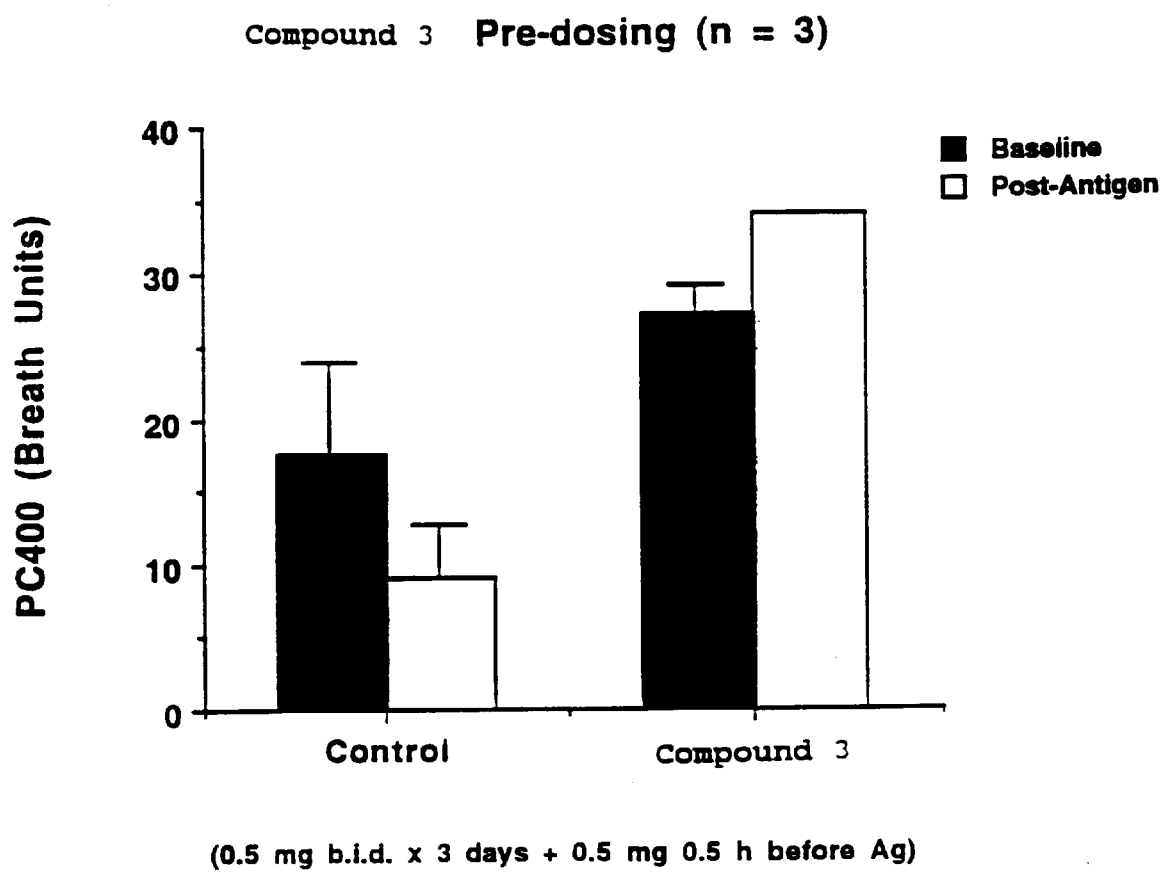
FIG. 8 is a bar chart showing the airway hyperresponsiveness (measured as PC400) antigen-challenged sheep pretreated with cis-1,5-cyclooctylene bis[4(4-guanidinobenzylcarbamoyl)-1-piperazinecarboxylate] (Compound 3) by aerosol administration of 0.5 mg per day for three days, with an additional 0.5 mg dose one half hour before antigen challenge, versus sheep treated with a control.

Aerosol treatment with Compound 3 prior to antigen challenge was also found to be effective in attenuating the early and late responses to the antigen challenge as measured by Specific Lung Resistance (SRL). For these studies, the animals were predosed, by aerosol administration, with Compound 3 (0.5 mg/day×3 days, with an additional 0.5 mg one half hour before antigen challenge). FIG. 7 shows a significant attenuation of early and late phase response to antigen challenge resulting from pretreatment with Compound 3. FIG. 8, likewise shows a significant improvement in airway function.

Thus, the present invention provides compounds and compositions that are useful for the prevention and treatment of immunomediated inflammatory disorders, particularly those associated with the respiratory tract, including asthma, and the hyperresponsiveness phase associated with chronic asthma, in addition to allergic rhinitis. The present invention is also recognized as providing a method for treating immunomediated inflammatory disorders that are susceptible to treatment with a compound of the present invention.

The disclosures in this application of all articles and references, including patents and patent applications, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A compound of the formula:

$$[Z-X^1-X^2-X^3-X^4-X^5]_2Y$$

in which:

Z is amino, guanidino or amidino;

Y is optionally substituted heterocyclo($C_{3-14}$)alkylene containing one or more oxygen atoms;

$X^1$ is optionally substituted ($C_{3-6}$)alkylene, optionally substituted oxa($C_{4-6}$) alkylene or —$X^6$—$X^7$—$X^8$— (wherein $X^7$ is optionally substituted phenylene, optionally substituted cyclo($C_{3-6}$)alkylene or optionally substituted heterocyclo($C_{3-6}$)alkylene and $X^6$ and $X^8$ are optionally substituted ($C_{n6}$)alkylene and optionally substituted heterocyclo($C_{n8}$)alkylene, respectively, wherein the sum of n6 and n8 is equal to 1, 2, 3 or 4, with the proviso that when Z is amino n6 is not 0);

$X^2$ and $X^4$ are independently —C(O)—, —C(O)O—, —OC(O)—, —C(O)N($R^1$)—, —N($R^1$)C(O)—, —OC(O)N($R^1$)—, —N($R^1$)C(O)O—, —N($R^1$)C(O)N($R^1$)— or —OC(O)O— (wherein each $R^1$ is independently hydrogen, optionally substituted ($C_{1-8}$)alkyl or optionally substituted cyclo($C_{3-8}$) alkyl);

$X^3$ is optionally substituted ($C_{1-8}$)alkylene, —$X^9$—$X^{10}$— or —$X^{10}$—$X^9$— (wherein $X^9$ is optionally substituted ($C_{n9}$)alkylene, wherein n9 is 0, 1 or 2, and $X^{10}$ is optionally substituted cyclo($C_{3-8}$)alkylene or optionally substituted heterocyclo($C_{3-8}$)alkylene, with the proviso that covalent bonds do not occur between hetero atoms contained within $X^{10}$ and hetero atoms contained within either $X^2$ or $X^4$); and $X^5$ is optionally substituted ($C_{n5}$)alkylene wherein n5 is 0, 1 or 2; and the pharmaceutically acceptable salts thereof.

2. The compound of claim 1 in which $X^2$ is —C(O)—, —C(O)NH—, —NHC(O)— or —NHC(O)O— and $X^4$ is —C(O)— or —C(O)O—.

3. The compound of claim 2 in which Y is dioxabicyclo [3.3.0] octylene.

4. The compound of claim 3 in which $X^3$ is 1,4-piperazinylene, 1,4-piperidylene, 1,4-perhydro-7H-1,4-diazepinylene or —$X^9$—$X^{10}$— (wherein $X^9$ is methylene and $X^{10}$ is 1,4-piperidylene) and $X^4$ is —C(O)— or —C(O)O—; or $X^3$ is ($C_{1-4}$)alkyene and $X^4$ is —N($R^1$)C(O)O— (wherein $R^1$ is hydrogen or methyl).

5. The compound of claim 4 in which n8 and n5 are independently 0 or 1.

6. The compound of claim 5 in which n5 is 0 and Y is 4,8-dioxabicyclo[3.3.0]octylene.

7. The compound of claim 6 in which Z is guanidino, $X^1$ is —$X^6$—$X^7$—$X^8$— (wherein n6 is 0, n8 is 1 and $X^7$ is 1,4-phenylene), $X^2$ is —NHC(O)—, $X^3$ is 1,4-piperazinylene, $X^4$ is —C(O)O— and Y is cis-2,6-(4,8-dioxabicyclo[3.3.0]octylene), namely cis-2,6-(4,8-dioxabicyclo[3.3.0]octylene) bis[4-(4-guanidinobenzylcarbamoyl)-1-piperazinecarboxylate] and the pharmaceutically acceptable salts thereof.

8. A compound of the formula:

$$R^2-Y-R^3$$

in which $R^2$ and $R^3$ are independently Z—$X^1$—$X^2$—$X^3$—$X^4$—$X^5$— in which:

Z is amino, guanidino or amidino;

Y is optionally substituted heterocyclo($C_{3-14}$)alkylene; containing one or more oxygenatoms;

$X^1$ is optionally substituted ($C_{3-6}$)alkylene, optionally substituted oxa($C_{4-6}$)alkylene or —$X^6$—$X^7$—$X^8$— (wherein $X^7$ is optionally substituted phenylene, optionally substituted cyclo($C_{3-6}$)alkylene or optionally substituted heterocyclo($C_{3-6}$)alkylene and $X^6$ and $X^8$ are optionally substituted ($C_{n6}$)alkylene and optionally substituted ($C_{n8}$)alkylene, respectively, wherein the sum of n6 and n8 is equal to 1, 2, 3 or 4, with the proviso that when Z is amino n6 is not 0);

$X^2$ and $X^4$ are independently —C(O)—, —C(O)O—, —OC(O)—, —C(O)N($R^1$)—, —N($R^1$)C(O), —OC(O)N($R^1$)—, —N($R^1$)C(O)O—, —N($R^1$)C(O)N($R^1$)— or —OC(O)O— (wherein each $R^1$ is independently hydrogen, optionally substituted ($C_{1-8}$)alkyl or optionally substituted cyclo($C_{3-8}$)alkyl;

$X^3$ is optionally substituted ($C_{1-8}$)alkylene, —$X^9$—$X^{10}$— or —$X^{10}$—$X^9$— (wherein $X^9$ is optionally substituted ($C_{n9}$)alkylene, wherein n9 is 0, 1 or 2, and $X^{10}$ is optionally substituted cyclo($C_{3-8}$)alkylene or optionally substituted heterocyclo($C_{3-8}$)alkylene, with the proviso that covalent bonds do not occur between hetero atoms contained within $X^{10}$ and hetero atoms contained within either $X^2$ or $X^4$); and $X^5$ is optionally substituted ($C_{n5}$)alkylene wherein n5 is 0, 1 or 2; with the proviso that $R^2$ and $R^3$ are not identical; and the pharmaceutically acceptable salts.

9. The compound of claim 8 in which $X^2$ is —C(O)NH—, —NHC(O)— or —NHC(O)O— and $X^4$ is —C(O)—or —C(O)O—.

10. The compound of claim 9 in which Y is dioxabicyclo [3.3.0]octylene.

11. The compound of claim 10 in which $X^3$ is 1,4-piperazinylene, 1,4-piperidylene, 1,4-perhydro-7H-1,4-diazepinylene or —$X^9$—$X^1$O— (wherein $X^9$ is methylene and $X^{10}$ is 1,4-piperidylene) and $X^4$ is —C(O)— or —C(O) O—; or $X^3$ is ($C_{1-4}$)alkyene and $X^4$ is —N($R^1$)C(O)O— (wherein $R^1$ is hydrogen or methyl).

12. The compound of claim 11 in which n8 and n5 are independently 0 or 1.

13. A pharmaceutical composition comprising the compound of claim 1 in combination with a pharmaceutically acceptable carrier.

14. The composition of claim 13 wherein said pharmaceutical composition comprises a pharmaceutically acceptable topical carrier.

15. An oral composition for the treatment of immunomediated inflammatory disorders comprising the compound of claim 1 in a pharmaceutically acceptable carrier.

16. An aerosol composition for the treatment of immunomediated inflammatory disorders comprising the compound of claim 1 in an aerosolized pharmaceutically acceptable carrier solution or dry powder.

17. The aerosol composition of claim 16, wherein the inflammatory disorder is asthma.

18. The aerosol composition of claim 16, wherein the inflammatory disorder is allergic rhinitis.

19. The aerosol composition of claim 16 wherein said compound is present in the pharmaceutically acceptable carrier solution at a concentration between about 0.01 and 30 mg/ml.

20. The aerosol composition of claim 16 further comprising a β-adrenergic agonist compound.

21. An aerosol device, comprising the compound of claim 1 in a pharmaceutically acceptable carrier solution or dry powder, and a means for converting said solution or dry powder into an aerosol form suitable for inhalation.

22. The aerosol device of claim 21 further comprising a β-adrenergic agonist compound.

23. The aerosol device of claim 22 wherein said β-adrenergic agonist compound is selected from the group consisting of albuterol, terbutaline, formoterol, fenoterol and prenaline.

24. A method for treating an immunomediated inflammatory disorder of the respiratory tract of a mammal, said method comprising administering to said mammal an inhalant composition comprising the compound of claim 1 in an aerosolized pharmaceutically acceptable carrier solution or dry powder.

25. The method of claim 24 further comprising a adrenergic agonist compound.

26. The method of claim 25 wherein said β-adrenergic agonist compound is selected from the group consisting of albuterol, terbutaline, formoterol, fenoterol and prenaline.

27. A method for treating immunomediated inflammatory skin conditions in a mammal, said method comprising administering topically to said mammal a topical composition comprising a therapeutically effective amount of the compound of claim 1 in a pharmaceutically acceptable topical carrier.

28. A method of treating rheumatoid arthritis in a mammal, comprising administering to said mammal a therapeutically effective amount of a compound of claim 1 to thereby relieve said rheumatoid arthritis.

29. A method of treating conjunctivitis in a mammal, said method comprising administering to said mammal a therapeutically effective amount of the compound of claim 1 to thereby relieve said conjunctivitis.

30. A method of treating syncytial virus infections in a mammal said method comprising administering to said mammal a therapeutically effective amount of the compound of claim 1.

* * * * *